United States Patent [19]
Andersson et al.

[11] Patent Number: 6,063,360
[45] Date of Patent: *May 16, 2000

[54] FREE RADICALS COMPRISING BENZODITHIOLE DERIVATIVES

[75] Inventors: Sven Andersson, Lomma; Finn Radner, Lund; Anna Rydbeck, Staffanstorp; Rolf Servin, Malmö; Lars-Göran Wistrand, Lund; Mikkel Thaning, Malmö, all of Sweden

[73] Assignee: Nycomed Imaging A/S, Oslo, Norway

[*] Notice: This patent is subject to a terminal disclaimer.

[21] Appl. No.: 09/036,021

[22] Filed: Mar. 6, 1998

[30] Foreign Application Priority Data

Apr. 2, 1993 [GB] United Kingdom .................. 9307027
Aug. 9, 1995 [GB] United Kingdom .................. 95/18442
Jun. 20, 1996 [GB] United Kingdom .................. 9612931
Mar. 6, 1997 [GB] United Kingdom .................. 04669

[51] Int. Cl.$^7$ .......................... A61K 49/00; C07D 339/06
[52] U.S. Cl. ................................ 424/9.3; 549/31
[58] Field of Search ................................ 549/31; 424/9.3

[56] References Cited

U.S. PATENT DOCUMENTS 5,530,140  6/1996  Andersson et al. ...................... 549/31
5,728,370  3/1998  Andersson et al. ...................... 549/31

*Primary Examiner*—Deborah C. Lambkin
*Attorney, Agent, or Firm*—Bacon & Thomas

[57] ABSTRACT

The present invention relates to certain novel triaryl methyl free radicals and their use as image enhancing agents in magnetic resonance imaging (MRI) as well as to contrast media containing such radicals and to the use of such radicals and their non-radical precursors in the manufacture of MRI contrast media.

13 Claims, No Drawings

ABSTRACT

FREE RADICALS COMPRISING BENZODITHIOLE DERIVATIVES

FIELD OF THE INVENTION

The present invention relates to certain novel triaryl methyl free radicals and their use as image enhancing agents in magnetic resonance imaging (MRI) as well as to contrast media containing such radicals and to the use of such radicals and their non-radical precursors in the manufacture of MRI contrast media.

BACKGROUND OF THE INVENTION

MRI is a diagnostic technique that has become particularly attractive to physicians as it is non-invasive and does not involve exposing the patient under study to potentially harmful radiation, such as for example the X-radiation of conventional radiography.

This technique, however suffers from several serious drawbacks, including in particular the expense of manufacture and operation of the MRI apparatus, the relatively long scanning time required to produce an image of acceptable spatial resolution, and the problem of achieving contrast in the magnetic resonance (MR) images between tissue types having the same or closely similar imaging parameters, for example in order to cause a tissue abnormality to show up clearly in the images.

The expense of manufacture and operation of an MRI apparatus is closely associated with the strength of the magnetic field that the primary magnet in the apparatus is required to generate in order to produce images of acceptable spatial resolution in an acceptable time.

MR images are generated by manipulation of the MR signals detected from the sample, for example a human or animal body, placed in a magnetic field and exposed to pulses of radiation of a frequency (typically radiofrequency (RF)) selected to excite MR transitions in selected non-zero spin nuclei (the "imaging nuclei", which are generally water protons in body fluids) in the sample.

The amplitude of the induced MR signals is dependent upon various factors such as the strength of the magnetic field experienced by the sample, the temperature of the sample, the density of the imaging nuclei within the sample, the isotopic nature and chemical environment of the imaging nuclei and the local inhomogeneities in magnetic field experienced by the imaging nuclei.

Thus many techniques have been proposed for enhancing MR image quality, for example by increasing MR signal amplitude or by increasing the difference in MR signal amplitude between different tissue types.

The imaging parameters (nuclear density, $T_1$ and $T_2$) for tissues of interest may be altered and many proposals have been made for doing this by the administration of MRI contrast agents into patients under study (see for example U.S. Pat. Nos. 4,647,447 (Gries/Schering), 4,925,652 (Gries/Schering) and 4,863,715 (Jacobsen/Nycomed)). Where such MRI contrast agents are paramagnetic they produce significant reduction in the $T_1$ of the water protons in the body zones into which they are administered or at which they congregate, and where they are ferromagnetic or superparamagnetic (for example as suggested by Jacobsen) they produce a significant reduction in the $T_2$ of the water protons. In either case the result is enhanced (positive or negative) contrast in the MR images of such zones.

The contrast enhancement achievable by such agents in conventional MRI is relatively limited and it is generally not such as to allow a reduction in the image acquisition period or in the field strength of the primary magnet.

Utilisation of the spin transition coupling phenomenon known as dynamic nuclear polarisation or as the Overhauser effect to amplify the population difference between the ground and excited spin states of the imaging nuclei by the excitation of a coupled ESR transition in a paramagnetic species present in the sample being imaged has been described in U.S. Pat. No. 4,984,573 (Leunbach/Nycomed Innovation).

This new technique for generating a MR image of the sample, which is hereinafter termed Overhauser MRI (OMRI), involves exposing the sample to a first radiation of a frequency selected to excite nuclear spin transitions in selected nuclei in the sample (radiation which is generally of radiofrequency or thereabouts and thus for convenience will be referred to hereinafter as RF radiation) and also exposing the sample to a second radiation of a frequency selected to excite electron spin transitions coupled to nuclear spin transitions for at least some of the selected nuclei (radiation which is generally of microwave frequency or thereabouts and thus for convenience is referred to hereinafter as MW or UHF radiation), the MR images being generated from the resulting amplified MR signals (free induction decay signals) emitted by the sample.

The paramagnetic substance which possesses the ESR transition which couples with the NMR transition of the image nuclei may be naturally present within the imaging sample or more usually may be administered as an OMRI contrast agent.

A number of "oxygen free radicals" that is to say radicals where the unpaired electron or electrons are associated with the oxygen atom have been proposed as OMRI contrast agents including for example nitroxide stable free radicals, chloranil semiquinone radical and Fremy's salt (U.S. Pat. No. 4,984,573) and deuterated stable free radicals, in particular deuterated nitroxide stable free radicals (WO-A-90/00904).

Such radicals have not however been found to be entirely satisfactory due to problems associated with stability, toxicity or poor coupling of the electron and nuclear spin transitions.

In WO-A-91/12024 Nycomed Innovation AB proposed persistant carbon free radicals, i.e. radicals where the unpaired electron or electrons are primarily associated with carbon atoms, including triaryl methyl radicals, for use as OMRI contrast agents.

SUMMARY OF THE INVENTION

We have now found that a particular group of novel triaryl methyl radicals has certain advantageous properties making them particularly suitable for use as OMRI contrast agents.

Viewed from one aspect the present invention thus provides a radical compound of formula I

(where each group $Ar^1$, which may be the same or different is an optionally substituted aromatic group, preferably an optionally substituted 5–7 membered carbocyclic or heterocyclic aromatic ring optionally carrying one or more fused carbocyclic or heterocyclic rings, and at least one of said $Ar^1$ groups is a group $Ar^3$ of formula

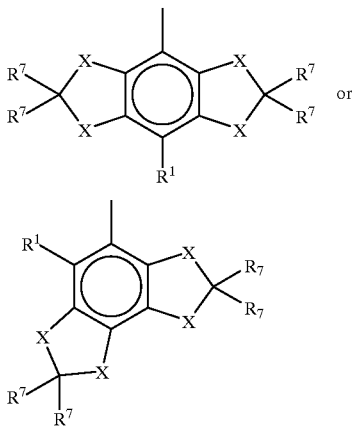

or

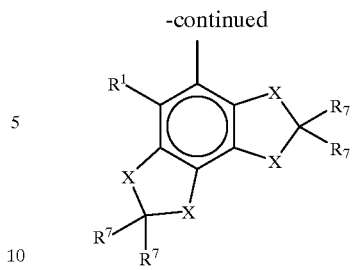

-continued (wherein each X which may be the same or different represents an oxygen or sulphur atom or a group CO or $S(O)_n$ (where n is 1 to 3) with the proviso that at least one group X is a sulphur atom or a $S(O)_n$ group;

$R^1$ represents a hydrogen atom or group of formula -M, -XM, -X-$Ar^2$, or -$Ar^2$ where M is a water solubilising group, and $Ar^2$ represents a 5–10 membered aromatic ring optionally substituted by a water solubilising group M; and each of the groups $R^7$, which may be the same or different represents a hydrogen atom, or a hydrocarbon group such as an alkyl, hydroxyalkyl, alkoxyalkyl, alkoxycarbonyl, or carbamoyl group, or a water solubilising group M or two groups $R^7$ together with the atom to which they are bound represent a carbonyl group or a 5 to 8 membered cycloalkylidene, mono- or di-oxacycloalkylidene, mono- or di-azacycloalkylidene or mono- or di-thiacycloalkylidene group optionally with the ring attachment carbon replaced by a silicon atom (preferably however in any spiro structure the ring linking atom will be bonded to no more than three heteroatoms) and $R^7$ where it is other than hydrogen, is optionally substituted by a hydroxyl group, an optionally alkoxylated, optionally hydroxylated acyloxy or alkyl group or a water solubilising group M)) or a salt thereof.

The optionally substituted aromatic group $Ar^1$ may be selected from any of the aromatic groups described for the triarylmethyl radicals of WO-A-91/12024.

Preferably however in compounds of Formula I where not all $Ar^1$ groups are groups $Ar^3$, those $Ar^1$ groups which are other than groups $Ar^3$ are groups $Ar^{1'}$ of formula

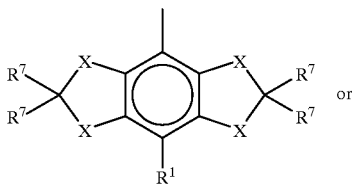

or (wherein X, $R^1$ and $R^7$ are as defined above excluding the proviso that at least one X is S or $S(O)_n$). In such preferred groups $Ar^{1'}$, X is preferably an oxygen atom and $R^7$ is a hydrogen atom or an optionally hydroxylated alkyl, preferably methyl group.

Preferred radical compounds of Formula I include those wherein at least one, preferably two, and more preferably all three $Ar^1$ groups are groups $Ar^3$ and any remaining $Ar^1$ groups are $Ar^{1'}$ groups.

Especially preferably in each group $Ar^3$ or $Ar^{1'}$, the two fused rings are the same.

In the radical compounds of formula I, the solubilising groups M may be any of the solubilising groups conventionally used in diagnostic and pharmaceutical products. Particularly preferred solubilizing groups M include optionally hydroxylated, optionally alkoxylated alkyl or oxo-alkyl groups and groups of formulae $R^5$, $COOR^5$, $OCOR^5$, CHO, CN, $CH_2S(O)R^5$, $CONR^5_2$, $NR^5COR^5$, $NR^5_2$, $SO_2NR^5_2$, $OR^5$, $PO_3^{2-}$, $SOR^5$, $SO_2R^5$, $SO_3M^1$, $COOM^1$ (where $R^5$ represents a hydrogen atom or an optionally hydroxylated, optionally aminated, optionally alkoxylated, optionally carboxylated alkyl, oxo-alkyl, alkenyl or alkaryl group and $M^1$ is one equivalent of a physiologically tolerable cation, for example an alkali or alkaline earth metal cation, an ammonium ion or an organic amine cation, for example a meglumine ion), —$(O(CH_2)_n)_mOR^5$ (where n is an integer having a value of from 1 to 3 and m is an integer having a value of from 1 to 5),

or $CH_2R^8$ (where $R^8$ is a hydrophilic $R^5$ group) or $SR^{10}$ or $SO_2R^{10}$ where $R^{10}$ is a group $R^5$ or an alkyl group optionally substituted by one or more, especially two or three groups $COOR^5$, $OCOR^5$, CHO, CN, $CONR^5_2$, $NR^5COR^5$, $NR^5_2$, $SO_2NR^5_2$, $OR^5$, $PO_3^{2-}$, $SOR^5$, $SO_2R^5$, $SO_3M^1$, $COOM^1$, or —$(O(CH_2)_n)_mOR^5$.

Especially preferred as solubilizing groups M are groups of formula $C(H)_{3-n}(CH_2OH)_n$, $R^9$, $COR^9$, $SR^9$, $SOR^9$, $SO_2R^9$, $CON(R^9)_2$, $NR^9_2$, $NHR^9$ and $CONHR^9$ [where $R^9$ may represent a hydroxylated alkyl group such as a group

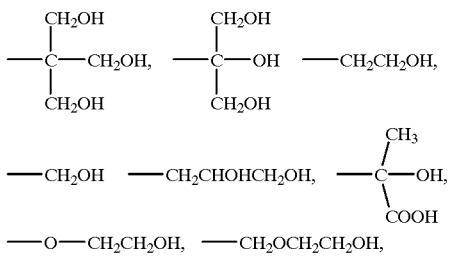

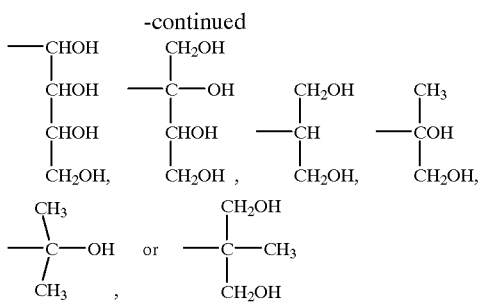

(although any $R^9$ group attached to a sulphur, nitrogen or oxygen atom is preferably not hydroxylated at the a carbon)], and groups of formula $SO_2R^{12}$ or $SR^{12}$ where $R^{12}$ is a group $CH_2COOR^{13}$, $CH(COOR^{13})_2$, $CH_2CONHR^9$, $CH_2CONR^9{}_2$, $CR^5(COOR^{13})_2$, $CH(CN)CO_2R^{13}$, $(CH_2)_nSO_3{}^-M^1$, $(CH_2)_nCOR^{13}$, $CH(COR^9)CH_2COR^9$ and $CH(R^5)COR^9$ where n, $M^1$ and $R^5$ are as earlier defined and $R^{13}$ is a hydrogen atom, an alkyl group or a group $M^1$ or $R^9$.

In the radical compounds of formula I any alkyl or alkenyl moiety preferably contains up to 6, especially preferably up to 4, carbon atoms and generally it is preferred for each of the three aryl monomers of the triaryl structure to be identical.

In groups $Ar^3$ according to the invention, group X is preferably selected from oxygen or sulphur atoms or $SO_2$ groups.

Within each $Ar^3$ moiety, preferably two and especially preferably all four X groups are sulphur atoms or $S(O)_n$ groups, preferably sulphur atoms or $SO_2$ groups.

Suitable $Ar^3$ groups thus include for example those wherein the central aromatic ring carries fused rings of formula

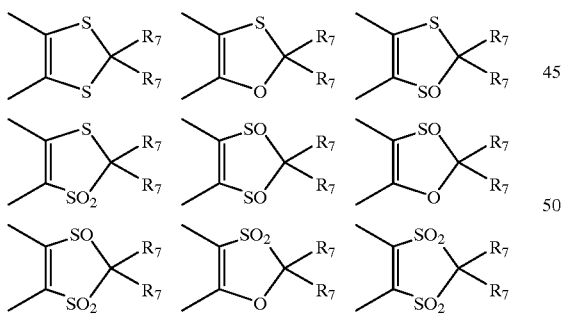

Preferred $Ar^3$ groups include

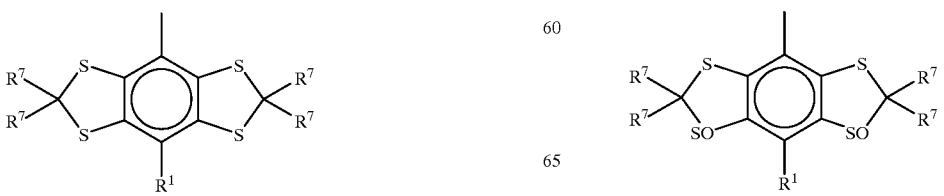

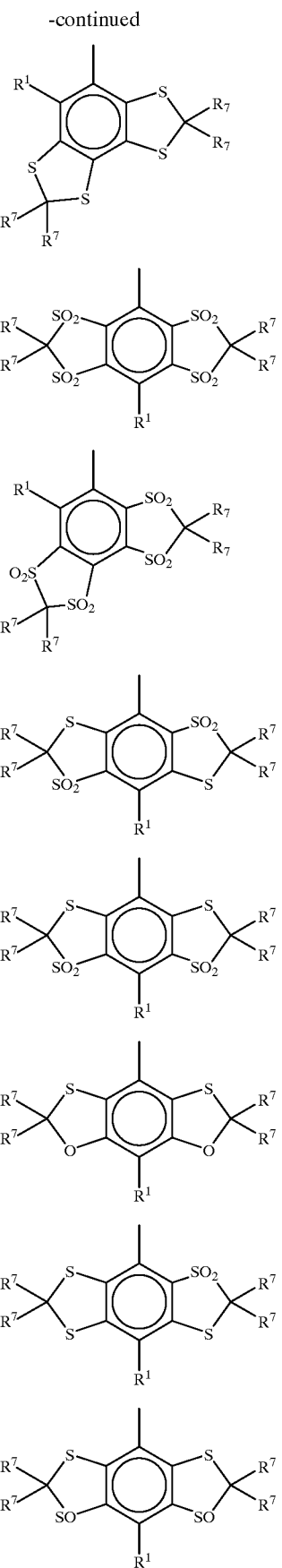

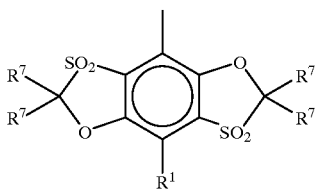

Within such preferred $Ar^3$ groups, $R^7$ is preferably a hydrogen atom or an optionally hydroxylated alkyl, preferably methyl group.

In the radical compounds of formula I preferred identities for the group $R^1$ include:

—H   —SCH$_2$COO—Na+   —SO$_2$R$^2$   —SR$^2$

—SCH$_2$COOCH$_2$CH$_3$   —SO$_2$C(R$^2$)$_2$CH$_2$CHOHCH$_2$OH

—SO$_2$NR$^2$$_2$   —SO$_2$CH$_2$CON(R$^2$)$_2$

—SO$_2$—C—(CH$_2$CH$_2$OH)$_2$   —SO$_2$C—(CH$_2$CH$_2$OH)$_2$
         |                              |
         COOCH$_2$CH$_3$                 CH$_2$OH

—C—(CH$_2$CH$_2$OH)$_3$   —SO$_2$—C(H)(COOCH$_2$CH$_3$)$_2$

—CH$_2$CON(CH$_2$CH$_2$OH)$_2$

Preferred radical structures of formula I include radical compounds of formulae Ia, Ib, Ic and Id:

(Ia)
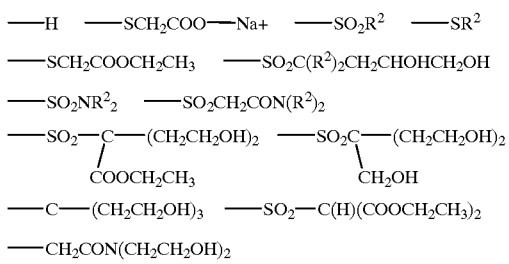

(Ib)

(Ic)

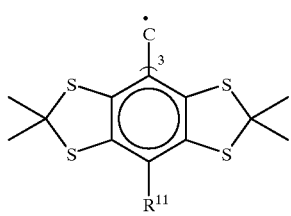

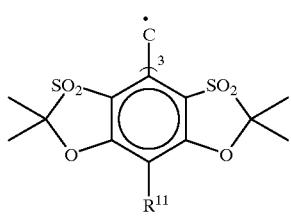

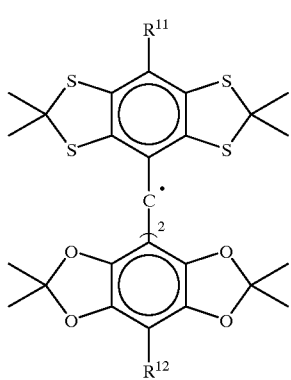

(Id)
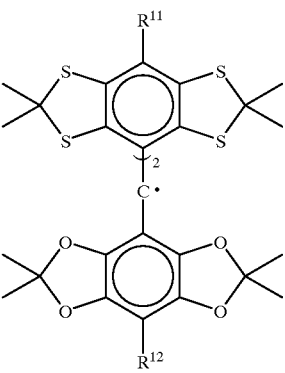

where $R^{11}$ and $R^{12}$ are selected from the list of preferred $R^1$ identities indicated above. Preferably $R^{11}$ and $R^{12}$ are selected from H, SCH$_3$, SCH$_2$CO$_2$CH$_2$CH$_3$, SCH$_2$COOH, SO$_2$N(CH$_3$)CH$_2$(CHOH)$_4$CH$_2$OH, SO$_2$NH$_2$, SO$_2$NCH$_2$CH$_2$OH and SO$_2$NCH$_2$CHOHCH$_2$OH, and particularly preferably $R^{11}$ and $R^{12}$ are identical.

Further aspects of the invention provide use of a compound of formula I for the manufacture of a contrast medium for use in OMRI and a method of magnetic resonance investigation of a sample, said method comprising introducing into said sample an inert carbon free radical, exposing said sample to a first radiation of a frequency selected to excite electron spin transitions in said free radical, exposing said sample to a second radiation of a frequency selected to excite nuclear spin transitions in selected nuclei in said sample, detecting free induction decay signals from said sample, and, optionally, generating an image or dynamic flow data from said detected signals.

Viewed from a still further aspect, the invention also provides a magnetic resonance imaging contrast medium composition comprising a radical compound of formula I together with at least one pharmacologically acceptable carrier or excipient.

For in vivo imaging, the radical compound should of course preferably be a physiologically tolerable radical, or one presented in a physiologically tolerable, e.g. encapsulated, form.

Viewed from a yet still further aspect the invention provides a method of magnetic resonance imaging wherein there is introduced into a human or non-human, preferably mammalian, subject an effective amount of a magnetic resonance signal amplifying agent and wherein an image of at least a part of said subject is generated, the improvement comprising introducing as said amplifying agent a radical according to the invention.

DETAILED DESCRIPTION

The novel triarylmethyl radicals of the invention have the advantages of the beneficial properties of stability at physiological pH, long half lives (at least one minute, and preferably at least one hour), long relaxation times, and surprisingly good relaxivity. Particularly advantageously, the novel radical compounds of the invention exhibit surprising stability when compared with corresponding compounds lacking $Ar^3$ groups as defined above. Stability is of paramount importance when considering suitability of radical compounds for use as MRI contrast agents, and thus the radical compounds of the present invention represent a considerable advance in the art.

Thus for example the radical compounds

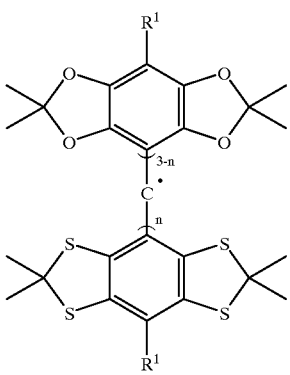

where n is 0, 1, 2 or 3 and $R^1$ is hydrogen, $SCH_3$, $SCH_2COOCH_2CH_3$ or $SCH_2COOH$ have been found to be at least 10 times more stable for each increment in n, e.g. the radical with n=3 is at least 1000 times more stable than the radical corresponding to n=0.

For use according to the invention free radicals which have relatively few transitions, e.g. less than 15, preferably less than 10, in their ESR spectra and radicals having narrow linewidth ESR transitions, e.g. up to 500 mG, preferably less than 150 mG, especially less than 60 mG and particularly less than 25 mG, are especially preferred for use as OMRI contrast agents. (The linewidths referred to are conveniently the intrinsic linewidths (full width at half maximum in the absorption spectrum) at ambient conditions).

Whilst low numbers of ESR transition lines are generally preferred to obtain more effective coupling of the ESR and NMR transitions, we have found that surprisingly good coupling, and therefore enhancement of the MR signal, may also be achieved with radicals showing a large number of ESR transitions.

Where the radicals have a multiplicity of ESR transitions, the hyperfine splitting constant is preferably very small. In this connection radicals having as few as possible non-zero spin nuclei, positioned as far away as possible from the paramagnetic centre are thus especially preferred.

The triarylmethyl radicals may be coupled to further molecules for example to lipophilic moieties such as long chain fatty acids or to macromolecules, such as polymers, proteins, polysaccharides (e.g. dextrans), polypeptides and polyethyleneimines. The macromolecule may be a tissue-specific biomolecule such as an antibody or a backbone polymer such as polylysine capable of carrying a number of independent radical groups which may itself be attached to a further macromolecule. Coupling to lipophilic molecules or substitution of the radical with lipophilic groups is particularly useful since it may enhance the relaxivity of the radicals in certain systems such as blood. Such lipophilic and macromolecular derivatives of the radicals of formula I and salts thereof form a further aspect of the present invention.

The linkage of a compound of formula I to the further molecule may be effected by any of the conventional methods such as the carbodiimide method, the mixed anhydride procedure of Krejcarek et al. (see Biochemical and Biophysical Research Communications 77:581 (1977)), the cyclic anhydride method of Hnatowich et al. (see Science 220:613 (1983) and elsewhere), the backbone conjugation techniques of Meares et al. (see Anal. Biochem. 142:68 (1984) and elsewhere) and Schering (see EP-A-331616 (Deutsch/Schering) for example) and by the use of linker molecules as described for in U.S. Pat. No. 5,208,324 (Klaveness/Nycomed).

In view of their surprisingly beneficial properties, the novel triarylmethyl radicals of the invention may also be used as conventional MRI contrast agents, as ESR contrast agents or as ESR spin labels in ESR imaging or in magnetometry.

The radical compounds of formula I may be prepared from their non-radical precursor compounds by conventional radical generation methods. Suitable non-radical precursor compounds include the corresponding triaryl methanes, triaryl methyl halides and triaryl methanols, and derivatives, e.g. ethers, of the triaryl methanols.

Thus in a further aspect the invention provides a process for the preparation of the radical compounds of formula I which comprises subjecting a radical precursor therefor to a radical generation step and optionally subsequently modifying the substitution on the aryl moieties, e.g. by oxidation or reduction. By such modification for example sulphide substituents, (e.g. $—SCH_3$ or —SCH COOEt) may be oxidized to the corresponding sulphones so avoiding problems of acidic hydrogens prior to radical formulation. Similarly lipophilic substituents (such as $—SCH_2COOEt$) may be reduced to corresponding hydrophilic substituents (e.g. $—SCH_2CH_2OH$).

Thus by way of illustration the radical-precursor can be represented by formula II $$(Ar^1)_3 CLv \qquad (II)$$

where $(Ar^1)_3C$ is as previously defined and Lv is a group displaceable to produce a radical. Formula II embraces formulae such as

| | |
|---|---|
| $(Ar^1)_3COH$ | (III) |
| $(Ar^1)_3CHal$ | (IV) |
| $(Ar^1)_3CH$ | (V) |
| $(Ar^1)_3CCOOH$ | (VI) |
| $(Ar^1)_3C.CO.O.O.CO.C(Ar^1)_3$ | (VII) |
| $(Ar^1)_3C.NN\ C(Ar^1)_3$ | (VIII) |

(Where Hal represents halogen, e.g. Br or Cl).

Thus for example radical compounds of formula I may conveniently be prepared from corresponding triaryl methyl halides by reduction with a metal catalyst, such as copper, zinc or silver, or by electrolytic reaction on an electrode or by photochemical reaction in the presence of a chlorine radical scavenger, e.g. an olefin. Alternatively, the radicals may be prepared from the corresponding triaryl methanes by reaction with a base, e.g. in the presence of sodium hydride followed by a reaction with an oxidant, e.g. iodine in the presence of oxygen or a quinone such as chloranil, following for example the method described in U.S. Pat. No. 3,347,941. Another method to prepare the radicals is to react triarylmethanes with other, less stable radicals such as tert-butoxyl radicals. The latter radicals are generated in situ via thermolysis or photolysis of an appropriate precursor, such as a peroxide or an azo compound. A further example of a method by which radical preparation may be effected is reaction of the corresponding triaryl methanols in the presence of an acid to form a carbonium ion followed by reduction to the free radical in the presence of a suitable reducing agent, such as metal ions e.g. $Cr^{2+}$, $Fe^{2+}$, or by electrochemical reduction. The carbon free radicals may also be generated by a comproportionation reaction between cations and anions of a corresponding radical precursor. In such a reaction an electron is exchanged between the anion and the cation, and two radicals are generated. Triarylmethyl radicals may thus be prepared by mixing together a triarylmethyl radical precursor cation with a corresponding anion. Triarylmethyl radicals may also be prepared by thermolysis or photolysis or a corresponding dimeric triarylmethyl structure, for example an azobistriarylmethyl or a bis(triarylmethylcarboxylic acid) peroxide. An alternative method of preparation of triarylmethyl radicals is the electrochemical decarboxylation of a triarylmethylcarboxylate.

Radicals with long half lives in aqueous solution, for example at least one hour, preferably ten days, more preferably fifty days and especially preferably at least one year are particularly desirable for use in in vivo imaging.

The non-radical precursors may themselves be prepared by methods conventional in the art and a number of suitable methods are described in WO-A-91/12024.

The documents referred to herein are incorporated herein by reference.

Thus for example the following reaction schemes may be used:

SCHEME 1:

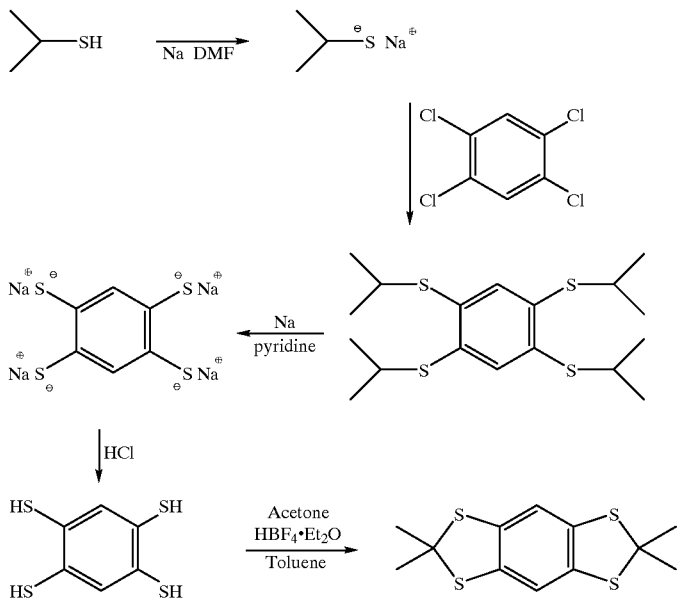

SCHEME 2:

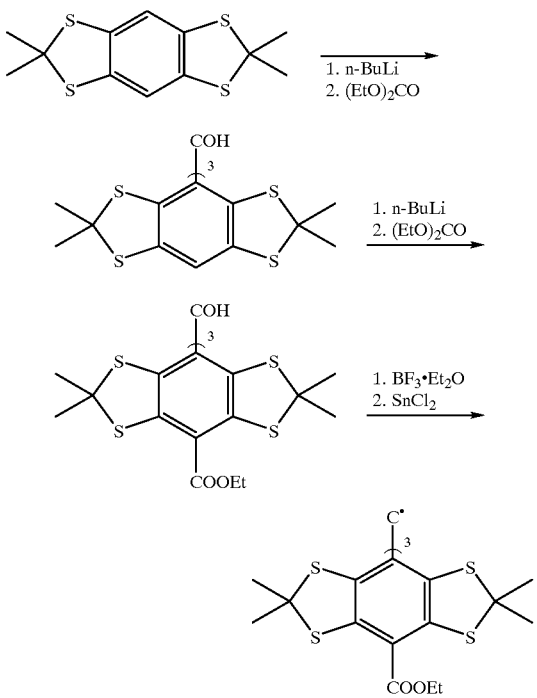

SCHEME 3:
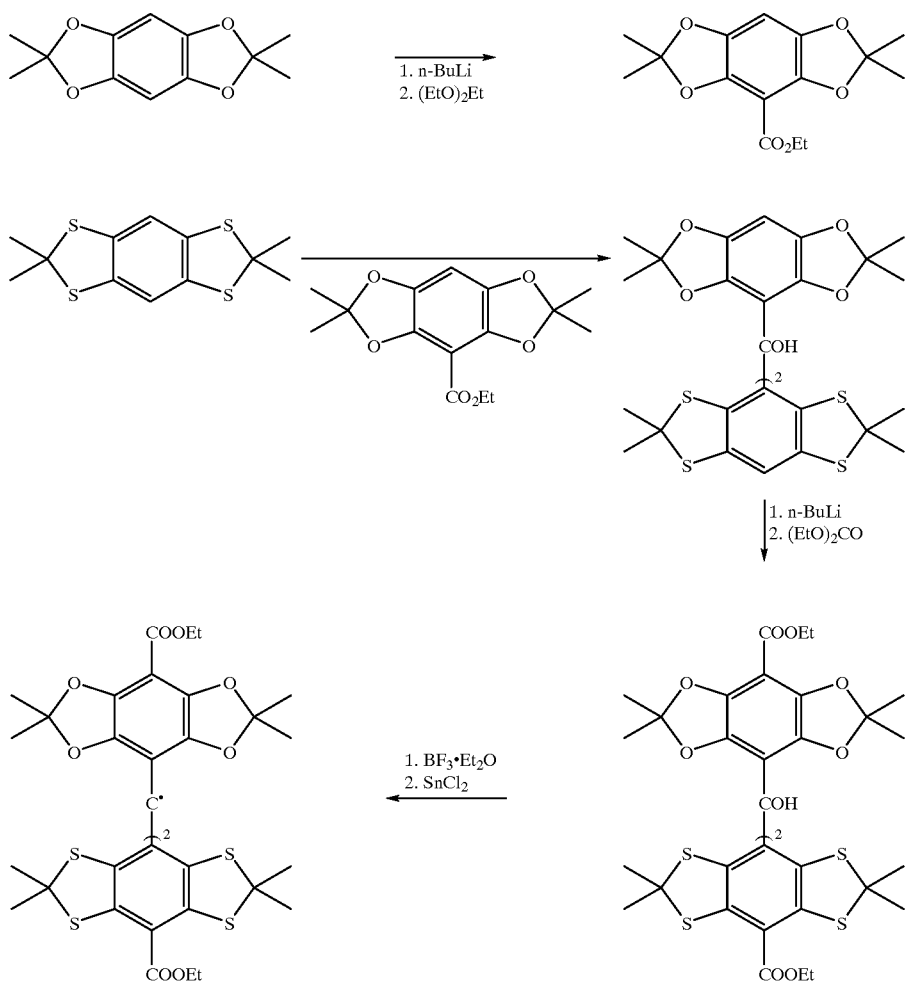
SCHEME 4:
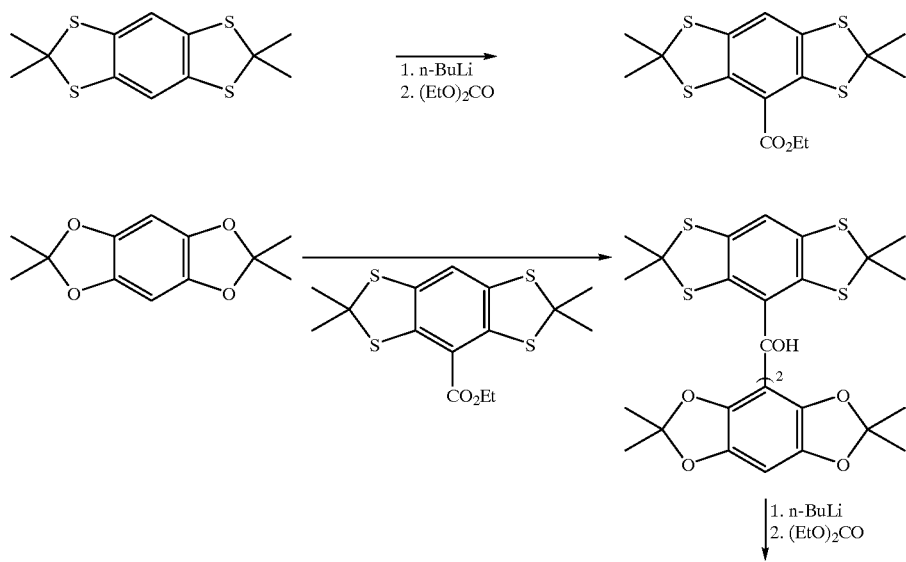

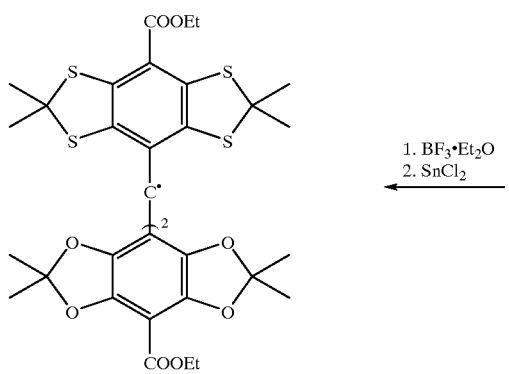
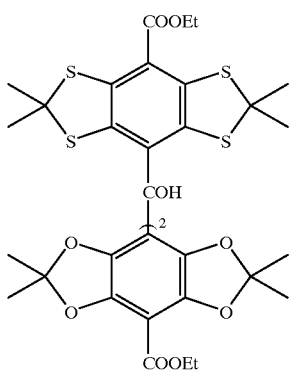

SCHEME 5:

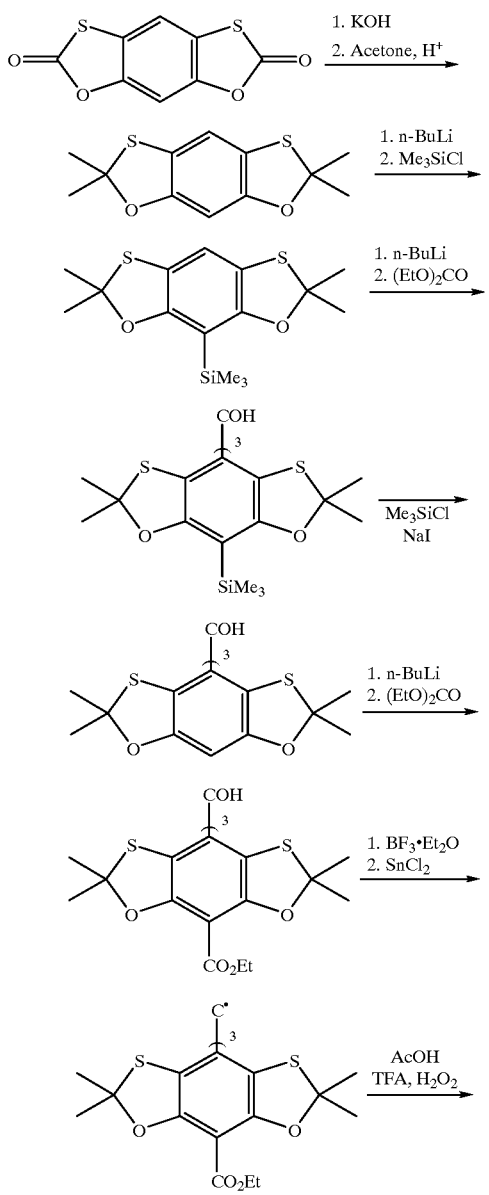

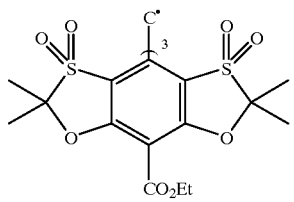

For use in OMRI, the radical compounds of formula I are conveniently formulated into contrast media together with conventional pharmaceutical carriers or excipients. Contrast media manufactured or used according to this invention may contain, besides the inert free radicals (or the non-radical precursor where radical formation is to be effected immediately before administration), formulation aids such as are conventional for therapeutic and diagnostic compositions in human or veterinary medicine. Thus the media may for example include solubilizing agents, emulsifiers, viscosity enhancers, buffers, etc. The media may be in forms suitable for parenteral (e.g. intravenous) or enteral (e.g. oral) application, for example for application directly into body cavities having external voidance ducts (such as the gastrointestinal tract, the bladder and the uterus), or for injection or infusion into the cardiovascular system. However solutions, suspensions and dispersions in physiological tolerable media will generally be preferred.

Free radicals which are relatively unstable or insoluble in the sample environment may be encapsulated, e.g. in gastric juice resistant capsules containing a medium in which they are stable. Alternatively, the radical may be presented as an encapsulated freeze dried powder in a soluble capsule. Such formulations might conveniently be dissolved shortly before in vivo use.

For use in in vivo diagnostic imaging, the medium, which preferably will be substantially isotonic, may conveniently be administered at a concentration sufficient to yield a 1 micromolar to 10 mM concentration of the free radical in the imaging zone; however the precise concentration and dosage will of course depend upon a range of factors such as toxicity, the organ targetting ability of the contrast agent, and the administration route. The optimum concentration for the free radical represents a balance between various factors. In general, optimum concentrations would in most cases lie in the range 0.1 to 100 mM, especially 0.2 to 10 mM, more especially 0.5 to 5 mM. Compositions for intravenous administration would preferably contain the free radical in concentrations of 10 to 1000 mM especially 50 to 500 mM.

For ionic materials, the concentration will particularly preferably be in the range 50 to 200 mM, especially 130 to 170 mM and for non-ionic materials 200 to 400 mM, especially 290 to 330 mM. For imaging of the urinary tract or the renal or biliary system however, compositions may perhaps be used having concentrations of for example 10 to 100 mM for ionic or 20 to 200 mM for non-ionic materials. Moreover for bolus injection the concentration may conveniently be 0.1 to 100 mM, preferably 5 to 25 mM, especially preferably 6 to 15 mM.

The present invention will now be further illustrated by the following non-limiting Examples (percentages, parts and ratios are by weight and temperatures are in degrees Celsius unless otherwise stated).

EXAMPLE 1

2,2,6,6-Tetramethylbenzo [1,2-d:4,5-d']-bis(1,3) dioxole-4-carboxylic Acid

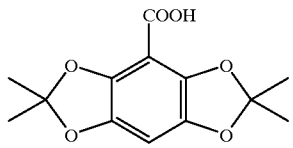

2,2,6,6-Tetramethylbenzo[1,2-d:4,5-d']-bis(1,3)dioxole (10.0 g, 45.0 mmol; prepared according to WO-91/12024) was dissolved in dry THF (200 mL) under an argon atmosphere. The solution was cooled to −20° C. and n-butyllithium (20.0 mL, 50.0 mmol) in hexane was added. After attaining ambient temperature, the reaction mixture was transferred onto solid carbon dioxide (150 g) and allowed to stand overnight. Water (200 mL) was added and pH was adjusted to 10 using 2M aqueous NaOH. After washing with ether, the aqueous phase was acidified with 2M hydrochloric acid to pH 2 and extracted with ether (2*300 mL). The organic phases were dried ($Na_2SO_4$) and evaporated to give the pure product. Yield: 10.7 g (89%).

1H NMR ($CDCl_3$, 300 MHz) δ: 6.50 (s, 1H), 1.71 (s, 12H). $^{13}$C NMR ($CDCl_3$ 75 MHz) δ: 165.1, 140.9, 140.8, 119.8, 98.9, 97.3, 25.6.

EXAMPLE 2

2,2,6,6-Tetramethylbenzo[2-d:4,5-d'-']-bis(1,3) dioxole-4-carboxylic Acid Methyl Ester

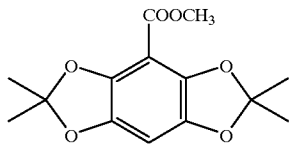

2,2,6,6-Tetramethylbenzo[1,2-d:4,5-d']-bis(1,3)dioxole-4-carboxylic acid (10.0 g, 38.0 mmol) was dissolved in dry DMF (100 mL). Potassium carbonate (15.2 g, 110.0 mmol) was added and the reaction was heated to 55° C. for 30 min. After cooling to ambient temperature, methyl iodide (15.6 g, 110.0 mmol) was added and the solution was stirred overnight. The precipitate was filtered off and the solution was evaporated. The residue was dissolved in saturated aqueous $NaHCO_3$ and ether. The aqueous layer was discarded and the organic phase was dried ($Na_2SO_4$), filtered and evaporated to give 9.4 g (88%) of the pure product.

$^1$H NMR ($CDCl_3$ 300 MHz) δ: 6.44 (s, 1H), 3.85 (s, 3H), 1.65 (s, 12H). $^{13}$C NMR ($CDCl_3$ 75 MHz) δ: 163.4, 140.8, 140.6, 119.0, 99.9, 99.4, 51.9, 25.6.

EXAMPLE 3

Bis-(2,2,6,6-tetramethylbenzo[1,2-d:4,5-d']-bis(1,3)-dithiole-4-yl)-mono-(2,2,6,6-tetramethylbenzo[1,2-d:4,5-d']-bis(1,3)dioxole-4-yl)methanol

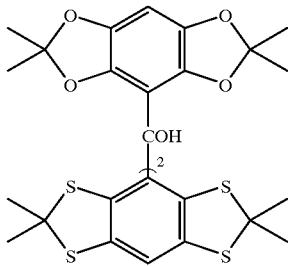

2,2,6,6-Tetramethylbenzo[1,2-d:4,5-d']bis(1,3)dithiole (2.86 g, 10 mmol; prepared according to WO-91/12024) was dissolved in anhydrous THF (75 mL) and cooled to −70° C. n-Butyllithium (4.4 mL, 2.5M in hexane) was added. The reaction mixture was allowed to reach ambient temperature. 4-Methoxycarbonyl-2,2,6,6-tetramethylbenzo[1,2-d:4,5-d']-bis-(1,3)-dioxole (1.4 g, 5 mmol) was added as a solid. After 1 hour, the mixture was quenched with saturated aqueous $NaH_2PO_4$. The aqueous phase was discarded and the organic layer evaporated. The residue was dissolved in dichloromethane, washed with water and dried ($Na_2SO_4$). The product was purified by column chromatography (dichloromethane:heptane, 1:1) giving 1.8 g (44%) of pure product.

$^1$H NMR ($CDCl_3$, 300 MHz) δ: 7.10 (broad s, 2 H, ArH), 6.39 (s, 1 H, ArH), 4.79 (s, 1 H, OH), 1.82–1.56 (m, 24 H. $CH_3$), 1.53 (s, 6 H, $CH_3$), 1.46 (s, 6 H, $CH_3$).

EXAMPLE 4

Bis-(2,2,6,6-tetramethylbenzo[1,2-d:4,5-d']-bis(1,3) dithiole-4-yl)-mono-(2,2,6,6-tetramethylbenzo[1,2-d:4,5-d']-bis(1,3)dioxole-4-yl)methyl

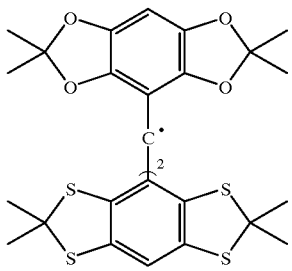

Bis-(2,2,6,6-tetramethylbenzo[1,2-d:4,5-d']-bis(1,3) dithiole-4-yl)-mono-(2,2,6,6-tetramethylbenzo[1,2-d:4,5-d']-bis(1,3)dioxole-4-yl)methanol (15.0 mg, 0.018 mmol) was dissolved in dichloromethane (0.8 mL) and $BF_3$.EtO (6.6 μL, 0.054 mmol) was added. After a few minutes, tin(II) chloride (10 mg, 0.054 mmol) was added together with acetonitrile (0.4 mL). After 5 min, the mixture was poured into dichloromethane (50 mL) and was washed with water (2*50 mL). The organic phase was dried ($MgSO_4$), filtered and evaporated. The product was not purified, but was analyzed by ESR.

ESR (THF, 200 G) triplet, $a_H$=2.5 G, line width 400 mG.

EXAMPLE 5

Bis-(8-ethoxycarbonylmethylthio-2,2,6,6-tetramethylbenzo[1,2-d:4,5-d']-bis(1,3)dithiole-4-yl)-mono-(8-ethoxycarbonylmethylthio-2,2,6,6-tetramethylbenzo[1,2-d:4,5-d']-bis(1,3)dioxole-4-yl) methanol

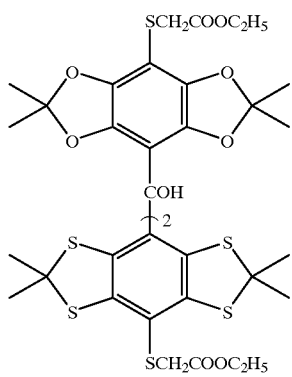

All reaction steps until the addition of ethyl bromoacetate were performed under an argon atmosphere using degassed solvents. Bis-(2,2,6,6-tetramethylbenzo[1,2-d:4,5-d']-bis(1,3)dithiol-4-yl)-mono-(2,2,6,6-tetramethylbenzo[1,2-d:4,5-d']bis(1,3)dioxole-4-yl)methanol (0.399 g, 0.486 mmol) was dissolved in dry benzene (9.0 mL). t-Butyllithium (2.0 mL, 1.5M in pentane) was added followed by tetramethyl ethylendiamine (TMEDA) (0.447 mL, 3.0 mmol). The mixture was stirred for 5 min and then treated with ultrasound for 30 min. S8 (0.100 g, 3.12 mmol) was added and the ultrasound treatment was continued for 2 h. The reaction was quenched by addition of aqueous 0.2M KOH (50.0 mL). After washing with benzene (40 mL), the aqueous phase was collected, ether (60 mL) was added and the aqueous phase was acidified using 2M hydrochloric acid. The organic phase was separated, filtered and evaporated. The residue was dissolved in degassed acetonitrile (40 mL). Ethyl bromoacetate (0.55 mL, 5.0 mmol) and potassium carbonate (1.0 g, 7.2 mmol) were added. The mixture was stirred overnight. The reaction was filtered and concentrated to 10 mL. A mixture of ether (50 mL) and aqueous NaH$_2$PO$_4$ (50 mL) was added. The organic phase was collected, dried (MgSO$_4$) and evaporated. The product was purified by preparative HPLC. Yield 83.2 mg (15%).

$^1$H NMR (CDCl$_3$, 300 MHz) δ: 4.71 (1H, s), 4.09–4.20 (6H, m), 3.53–3.65 (6H, m), 1.51–1.80 (36H, m), 1.24–1.32 (9H, m).

EXAMPLE 6

Bis-(8-ethoxycarbonylmethylthio-2,2,6,6-tetramethylbenzo[1,2-d:4,5-d']-bis(1,3)dithiol-4-yl)-mono-(8-ethoxycarbonylmethylthio-2,2,6,6-tetramethylbenzo[1,2-d:4,5-d']-bis(1,3)dioxole-4-yl) methyl

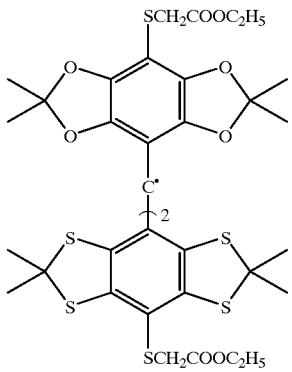

Bis-(8-ethoxycarbonylmethylthio-2,2,6,6-tetramethylbenzo [1,2-d:4,5-d']-bis(1,3)dithiole-4-yl)-mono-(8-ethoxycarbonylmethylthio-2,2,6,6-tetramethylbenzo[1,2-d:4,5-d']-bis(1,3)dioxol-4-yl) methanol (15 mg, 0.013 mmol) was dissolved in dichloromethane (0.8 mL) and BF$_3$ Et$_2$O (8.0 μL, 0.065 mmol) was added. Tin(II) chloride (12.3 mg, 0.065 mmol) and acetonitrile (0.4 mL) was added to this mixture. After aqueous workup and evaporation, the product was purified by preparative HPLC. Yield: 13 mg (85%). ESR (THF, 200 G):triplet, $a_H$=100 mG, linewidth 73 mG. Overhauser enhancement (THF, 2.1 mM): 195 at 2.13 W microwave power. Stability measurements: Half life in acetonitrile without exclusion of air: 2700 h.

EXAMPLE 7

Bis-(8-sodium carboxylate methylthio-2,2,6,6-tetramethylbenzo[1,2-d:4,5-d']-bis(1,3)dithiole-4-yl)-mono-(8-sodium carboxylate methylthio-2,2,6,6-tetramethylbenzo[1,2-d;4,5-d']-bis(1,3)dioxole-4-yl) methyl

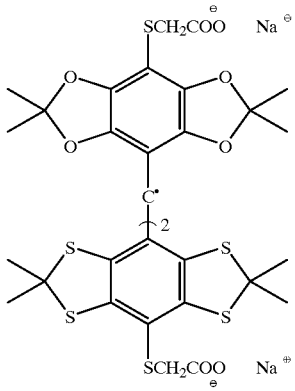

Bis-(8-ethoxycarbonylmethylthio-2,2,6,6-tetramethylbenzo[1,2-d:4,5-d']-bis(1,3)dithiole-4-yl)-mono-(8-ethoxycarbonylmethylthio-2,2,6,6-tetramethylbenzo[1,2-d:4,5-d']-bis(1,3)dioxole-4-yl)methyl (9 mg, 0.008 mmol) was dissolved in ethanol (25 mL). Water (5 mL) and 1M NaOH (48 μL, 0.048 mmol) was added and the reaction was stirred for 1 h at 35° C. The solution was evaporated. The product was purified by preparative HPLC. The collected fractions was evaporated, dissolved in water and ether. The ether layer was evaporated and the residue was dissolved in water and TM NaOH (24 μL, 0.024 mmol). The solution was lyophilized. Yield: 7 mg (75%). ESR (water, 5 mM, 200 G): singlet, linewidth 73 mG. Overhauser enhancement (water, 5 mM): 179 at 1.1 W microwave power. Stability measurements: Half life in water without exclusion of air: 60 h.

EXAMPLE 8

Bis-(8-sodium carboxylate ($2H_2$)methylthio-2,2,6,6-tetramethylbenzo[1,2-d:4,5-d']-bis(1,3)dithiole-4-yl)-mono-(8-sodium carboxylate ($^2H_2$)methylthio-2,2,6,6-tetramethylbenzo[1,2-d:4,5-d']-bis(1,3)dioxole-4-yl)methyl

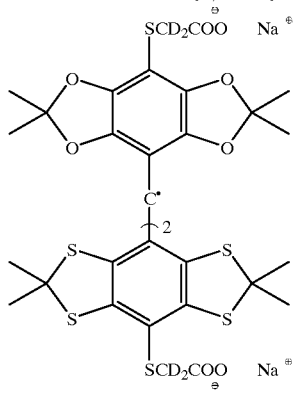

This radical was prepared using the procedure described in Example 7 from bis-(8-ethoxycarbonylmethylthio-2,2,6,6-tetramethylbenzo[1,2-d:4,5-d']-bis(1,3)dithiole-4-yl)-mono-(8-ethoxycarbonylmethylthio-2,2,6,6-tetramethylbenzo[1,2-d:4,5-d']-bis (1,3)dioxole-4-yl)methyl (9 mg, 0.008 mmol) in methanol-$d_1$ (25 mL), $D_2O$ (5 mL) and 1M NaOD (48 μL, 0.048 mmol). The product was purified by preparative HPLC and the pure product was lyophilized. Yield: 7 mg (75%). ESR ($H_2O$, 200 G): singlet, linewidth 86 mG. Overhauser enhancement ($H_2O$): 47 at 10 W microwave power.

EXAMPLE 9

Bis-(8-ethoxycarbonyl-2,2,6,6-tetramethylbenzo[1,2-d:4,5-d']-bis(1,3)dithiole-4-yl)-mono-(8-ethoxycarbonyl-2,2,6,6-tetramethylbenzo[1,2-d:4,5-d']-bis(1,3)dioxol-4-yl)methanol

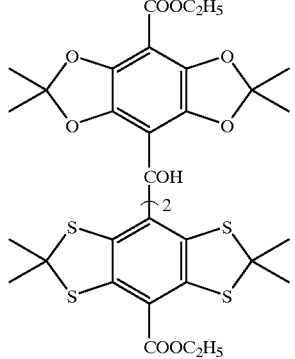

Bis-(2,2,6,6-tetramethylbenzo([1,2-d:4,5-d']-bis(1,3) dithiole-4-yl)-mono-(2,2,6,6-tetramethylbenzo[1,2-d:4,5-d']-bis(1,3)dioxol-4-yl)methanol (0.50 g, 0.61 mmol) was dissolved in dry benzene (6.0 mL) under an atmosphere of argon. t-Butyllitium (2.44 mL, 1.5M in pentane) and TMEDA (0.545 mL, 3.66 mmol) were added. The reaction mixture was subjected to ultrasound for 25 min. and was then slowly added to a solution of diethyl carbonate (7.2 mL, 59.4 mmol) in dry benzene (16 mL). After stirring for 1.5 h, aqueous $NaH_2PO_4$ (50 mL) was added. The organic layer was separated, washed with water, dried ($Na_2SO_4$) and evaporated. After purification by preparative HPLC 130.0 mg (21%)) of the pure product was obtained.

$^1H$ NMR ($CDCl_3$, 300 MHz) δ: 4.98 (s, 1H), 4.28–4.37 (m, 6H), 1.48–1.79 (m, 36H), 1.46 (t, 6H, J 7.0 Hz), 1.38 (t, 3H, J 7.0 Hz). $^{13}C$ NMR ($CDCl_3$, 75 MHz) δ: 166.2, 166.0, 162.9, 141.9, 141.6, 141.2, 140.8, 140.4, 140.0, 136.6, 134.5, 129.9, 128.5, 128.1, 127.8, 127.2, 120.3, 118.9, 111.9, 101.1, 80.6, 62.1, 61.0, 60.3, 60.2, 59.8, 59.2, 34.4, 34.3, 33.5, 28.8, 28.1, 27.0, 26.9, 26.5, 25.8.

EXAMPLE 10

Bis-(8-ethoxycarbonyl-2,2,6,6-tetramethylbenzo[1,2-d:4,5-d']-bis(1,3)dithiole-4-yl)-mono-(8-ethoxycarbonyl-2,2,6,6-tetramethylbenzo[1,2-d:4,5-d']-bis(1,3)dioxol-4-yl)methyl

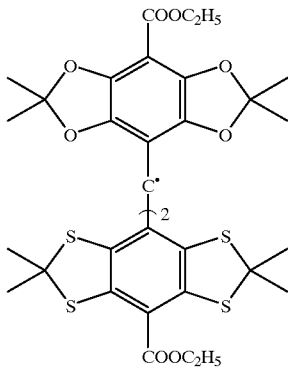

Bis-(8-ethoxycarbonyl-2,2,6,6-tetramethylbenzo[1,2-d:4,5-d']-bis(1,3)dithiol-4-yl)-mono-(8-ethoxycarbonyl-2,2,6,6-tetramethylbenzo[1,2-d:4,5-d']-bis(1,3)dioxol-4-yl) methanol (520 mg, 0.501 mmol) was dissolved in dry degassed dichloromethane (15 mL) together with tin(II) chloride (95 mg, 0.501 mmol) and acetonitrile (5 mL). $BF_3 \cdot EtO$ (70 μL, 0.557 mmol) was added and the solution was stirred for 20 min. After addition of dichloromethane (80 mL) and washing with degassed water (80 mL), the organic layer was separated, dried ($MgSO_4$), filtered and evaporated. The product was purified by preparative HPLC. Yield: 110 mg (22%). ESR (THF, 200 G) singlet, line width 325 mG. Overhauser enhancement (THF, 2.1 mM): 156 at 4 W microwave power. Stability measurements: Half life in acetonitrile without exclusion of air: 2000 h.

EXAMPLE 11

Bis-(8-potassium carboxylate-2,2,6,6-tetramethylbenzo[1,2-d:4,5-d']-bis(1,3)dithiol-4-yl)-mono-(8-potassium carboxylate-2,2,6,6-tetramethylbenzo[1,2-d:4,5-d']-bis(1,3)dioxol-4-yl)methyl

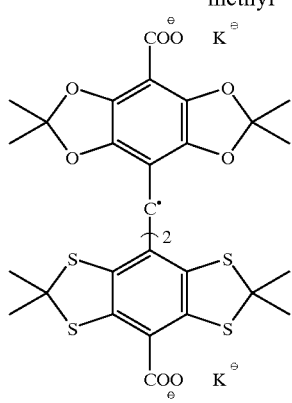

Bis-(8-ethoxycarbonyl-2,2,6,6-tetramethylbenzo[1,2-d:4,5-d']-bis(1,3)dithiol-4-yl) -mono-(8-ethoxycarbonyl-2,2,6,6-tetramethylbenzo[1,2-d:4,5-d']-bis(1,3)dioxol-4-yl) methyl (132 mg, 0.129 mmol) was dissolved in ethanol (10 mL). Aqueous potassium hydroxide (5 mL, 1.0M) was added and the reaction mixture was stirred at 50° C. overnight. After evaporation of the ethanol, the mixture was stirred for 1 h at 50° C. and was then acidified with 2M hydrochloric acid. The aqueous phase was extracted with ether. The organic phase was separated, dried (MgSO$_4$) filtered and evaporated. The product was purified by preparative HPLC. The fractions were evaporated and water was added. The aqueous layer was extracted with ether. The organic layer was separated, dried (MgSO$_4$), filtered and evaporated. The product was dissolved by adding water and 1M KOH (0.387 mL, 0.387 mmol). The solution was lyophilized. Yield: 101 mg (75%). ESR (H$_2$O, 200 G): singlet, line width 105 mG. Overhauser enhancement (H$_2$O, 0, 6.9 mM): 219 at 0.012 W microwave power.

EXAMPLE 12

Bis-(8-N,N-dimethylcarboxamide-2,2,6,6-tetramethylbenzo[1,2-d:4,5-d'-]-bis(1,3)dithiol-4-yl)-mono-(8-N,N-dimethylcarboxamide-2,2,6,6-tetramethylbenzo[1,2-d:4,5-d']-bis(1,3)dioxol-4-yl) methanol

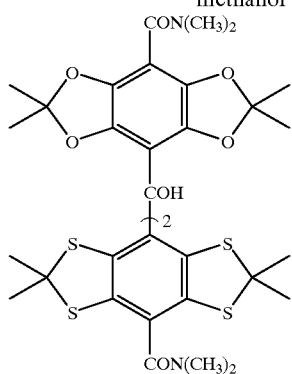

Bis-(2,2,6,6-tetramethylbenzo[1,2-d:4,5-d']-bis(1,3) dithiol-4-yl)-mono-(2,2,6,6-tetramethylbenzo[1,2-d:4,5-d'] bis(1,3)dioxol-4-yl)methanol (0.292 g, 0.356 mmol) was dissolved in dry benzene (7.0 mL) in an argon atmosphere. t-Butyllithium (1.45 mL, 1.5M in pentane) and TMEDA (0.325 mL, 2.18 mmol) were added. The solution was subjected to ultrasound for 30 min After cooling to 10° C., the reaction mixture was added to a solution of N,N-dimethyl carbamoylchloride (1.4 mL, 15.0 mmol) and t-butyllithium (0.25 mL, 1.5M in pentane) in dry benzene (20 mL). The mixture was stirred for 17 h and quenched with aqueous NaH$_2$PO$_4$. The organic layer was separated, washed with water, dried (Na$_2$SO$_4$) and evaporated. After purification by preparative HPLC 10.0 mg (3%) of the pure product was obtained.

$^1$H NMR (CDCl$_3$ 300 MHz) δ: 4.80 (s, 1H), 2.97–3.12 (m, 18H), 1.44–1.80 (m, 36H).

EXAMPLE 13

Bis-(8-dimethylaminocarbonyl-2,2,6,6-tetramethylbenzo[1,2-d:4,5-d']-bis(1,3)dithiol-4-yl)-mono-(8-dimethylaminocarbonyl-2,2,6,6-tetramethylbenzo[1,2-d:4,5-d']-bis(1,3)dioxol-4-yl)methyl

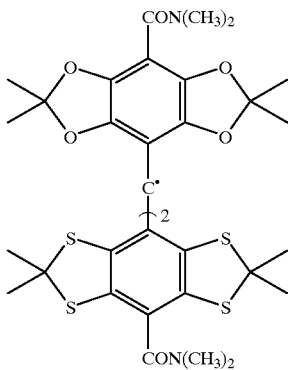

Bis-(8-dimethylaminocarbonyl-2,2,6,6-tetramethylbenzo[1,2-d:4,5-d']-bis(1,3)dithiol-4-yl)-mono-(8-dimethylaminocarbonyl-2,2,6,6-tetramethylbenzo[1,2-d:4,5-d']-bis(1,3)dioxol-4-yl)methanol (3 mg, 0.003 mmol) was dissolved in degassed acetonitrile (2 mL) under an atmosphere of argon. Tin(II) chloride (3 mg, 0.016 mmol) and BF$_3$.Et$_2$O (20 µL, 0.16 mmol) were added sequentially. The reaction mixture was stirred for 2 min and then transferred to a separatory funnel containing degassed ether (20 mL) and water (20 mL). The organic layer was separated, dried (MgSO$_4$), filtered and evaporated. No further purification was done. The yield was not determined. ESR (diethyl ether, 200 G): singlet, line width 535 mG. Overhauser enhancement (diethyl ether): 18 at 4 W microwave power.

EXAMPLE 14

4-Methoxycarbonyl-(2,2,6,6-tetramethylbenzo[1,2-d:4,5-d']-bis(1,3)dithiole)

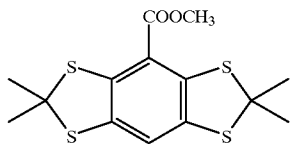

2,2,6,6-Tetramethylbenzo[1,2-d:4,5-d']-bis(1,3)dithiole (2.0 g, 6.98 mmol) was dissolved in dry ether (50.0 mL) in a dry, argon filled reaction flask. n-Butyllithium (3.07 mL, 2.5M in hexane) was added and the reaction mixture was stirred for 30 min. The solution was poured onto solid carbon dioxide and, after stirring overnight, the ether was filtered off. The solid residue was washed with chloroform and dried under vacuum. The crude product was mixed with potassium carbonate (0.97 g, 6.98 mmol) in dry DMF (20.0 mL) and was stirred for 1.5 h at 60° C. After cooling to ambient temperature, methyl iodide (0.435 mL, 6.98 mmol) was added. The stirring was continued overnight. The mixture was filtered, the solution evaporated and the residue was dissolved in dichloromethane and water. The organic phase was washed with water (2*30 mL), dried ($Na_2SO_4$) and evaporated to give after additional drying under vacuum a bright green-yellow crystalline pure product. Yield 1.56 g (65%).

$^1$H NMR ($CDCl_3$, 300 MHz) δ: 7.14 (s, 1H), 3.94 (s, 3H), 1.85 (s, 12 H). $^{13}$C NMR ($CDCl_3$, 75 MHz) δ: 140.1, 136.5, 118.2, 118.0, 117.6, 52.4, 25.6.

EXAMPLE 15

Bis-(2,2,6,6-tetramethylbenzo[1,2-d:4,5-d']-bis(1,3)dioxol-4-yl)-mono-(2,2,6,6-tetramethylbenzo[1,2-d:4,5-d']-bis(1,3)dithiole-4-yl)methanol

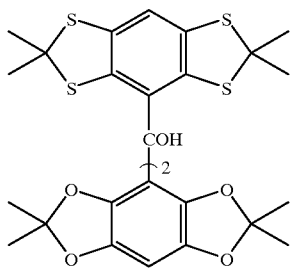

2,2,6,6-Tetramethylbenzo[1,2-d:4,5-d']-bis(1,3)dioxole (5.15 g, 23.2 mmol) was dissolved in dry ether (40.0 mL) in a dried, argon filled reaction vessel. The solution was cooled to 0° C. and n-butyllithium (9.29 mL, 2.5M in hexane) was added. After stirring for 15 min at ambient temperature, the mixture was cooled to 0° C. and 4-methoxycarbonyl-(2,2,6,6-tetramethylbenzo[1,2-d:4,5-d']-bis(1,3)dithiole) (4.0 g, 11.6 mmol) was added portionwise. The reaction was stirred at ambient temperature overnight. The voluminous precipitate was dissolved by addition of water (70 mL) and ether (50 mL). The organic layer was separated and the aqueous phase was washed once more with ether. The organic phase was dried ($Na_2SO_4$) and evaporated to give a semisolid residue. The product was recrystallized from acetonitrile. Yield of pure product was 5.26 g (60%).

$^1$H NMR ($CDCl_3$, 300 MHz) δ: 7.06 (s, 1H), 6.30 (s, 2H), 4.48 (s, 1H, OH), 1.29–1.86 (m, 36 H). 13C NMR ($CDCl_3$, 75 MHz) δ: 140.1, 139.6, 139.4, 136.5, 136.2, 120.2, 118.0, 117.6, 82.4, 25.8, 25.6, 25.2. MS (thermospray) m/z: 756 (M+).

EXAMPLE 16

Bis-(8-ethoxycarbonylmethylthio-2,2,6,6-tetramethylbenzo[1,2-d:4,5-d']-bis(1,3)dioxol-4-yl)-mono-(8-ethoxycarbonylmethylthio-2,2,6,6-tetramethylbenzo[1,2-d:4,5-d']-bis(1,3)dithiol-4-yl) methanol

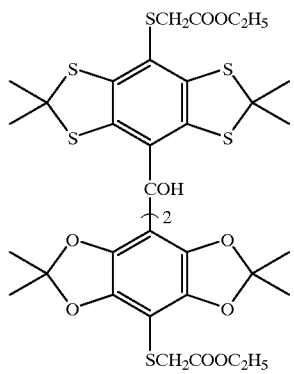

Bis-(2,2,6,6-tetramethylbenzo[1,2-d:4,5-d']-bis(1,3)dioxol-4-yl)-mono-(2,2,6,6-tetramethylbenzo[1,2-d:4,5-d']-bis(1,3)dithiol-4-yl)methanol (0.37 g, 0.489 mmol) was dissolved in dry THF (40 mL) under an atmosphere of argon. The solution was cooled to −20° C., n-butyllithium (0.78 mL, 2.5M in hexane) was added and the solution was stirred for 1 h. $S_8$ (0.050 g, 1.47 mmol) was added, the cooling bath was removed and the reaction was allowed to reach ambient temperature overnight. The reaction was again cooled to −20° C. and was treated with n-butyllithium (2.34 mL, 2.5M in hexane) for 1 h. $S_8$ (0.15 g, 4.41 mmol) was added, the cooling bath was removed and the reaction was stirred overnight at ambient temperature. A third time the reaction was cooled to −20° C., n-butyllithium (0.78 mL, 1.96 mmol) was added, stirred for 1 h and $S_8$ (0.050 g, 1.47 mmol) was added. The cooling bath was removed. After stirring for four hours the reaction mixture was quenched by the addition of a degassed ether/aqueous $NaH_2PO_4$ mixture. The organic phase was separated and the aqueous phase was washed once with ether. The organic phases were dried ($Na_2SO_4$) and evaporated to give a semi solid residue. Acetonitrile (50 mL), potassium carbonate (1.081 g, 7.82 mmol) and ethyl bromoacetate (0.868 mL, 7.82 mmol) were added. The mixture was stirred overnight, filtered and evaporated. After preparative HPLC 54.3 mg (10%) of the pure product was obtained.

$^1$H NMR (CDCl, 300 MHz) δ: 4.38 (s, 1H, OH), 4.05–4.20 (m, 6H), 3.59 (s, 4H), 3.53 (s, 2H), 1.34–1.75 (m, 36H), 1.16–1.33 (m, 9H). $^{13}$C NMR ($CDCl_3$, 75 MHz) δ: 168.8, 144.5, 136.2, 135.0, 119.5, 118.9, 117.7, 110.0, 97.9, 76.0, 61.2, 60.4, 35.5, 25.5, 14.1.

EXAMPLE 17

Bis-(8-ethoxycarbonylmethylthio-2,2,6,6-tetramethylbenzo[1,2-d:4,5-d']-bis(1,3)dioxol-4-yl)-mono-(8-ethoxycarbonylmethylthio-2,2,6,6-tetramethylbenzo[1,2-d:4,5-d']-bis(1,3)dithiol-4-yl) methyl

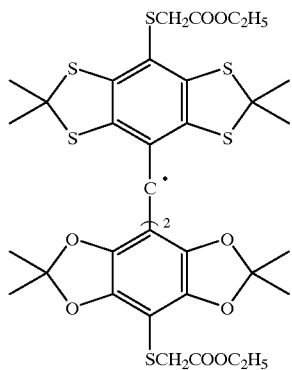

Bis-(8-ethoxycarbonylmethylthio-2,2,6,6-tetramethylbenzo[1,2-d:4,5-d']-bis(1,3)dioxol-4-yl)-mono-(8-ethoxycarbonylmethylthio-2,2,6,6-tetramethylbenzo[1,2-d:4,5-d']-bis(1,3)dithiol-4-yl)methanol (12.3 mg, 0.011 mmol) was dissolved in dry, degassed acetonitrile (2 mL) under an argon atmosphere. $BF_3 \cdot Et_2O$ (4.7 µL, 0.022 mmol) was added with stirring. Tin(II) chloride (5 mg, 0.022 mmol) was added followed by amalgamated zinc (2 mg, 0.030 mmol). The reaction was added to a mixture of degassed dichloromethane (40 mL) and water (30 mL). The organic layer was separated, dried ($Na_2SO_4$) and evaporated. The radical was purified by preparative HPLC. The yield was not determined. ESR (THF, 200 G): singlet, linewidth 222 mG. Overhauser enhancement (THF, 5.7 mM): 232 at 1.5 W microwave power. Stability measurements: Half life in acetonitrile without exclusion of air: 100 h.

EXAMPLE 18

Bis-(8-sodium carboxylate methylthio-2,2,6,6-tetramethylbenzo[1,2-d:4,5-d']-bis(1,3)dioxol-4-yl)-mono-(8-sodium carboxylate methylthio-2,2,6,6-tetramethylbenzo[1,2-d:4 5-d']-bis(1,3)dithiol-4-yl) methyl

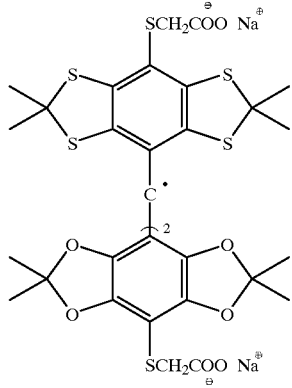

Bis-(8-ethoxycarbonylmethylthio-2,2,6,6-tetramethylbenzo [1,2-d:4,5-d']-bis(1,3)dioxol-4-yl)-mono-(8-ethoxycarbonylmethylthio-2,2,6,6-tetramethylbenzo[1,2-d:4,5-d']-bis(1,3)dithiol-4-yl)methyl (9 mg, 0.009 mmol) was dissolved in dry, degassed acetonitrile (1.5 mL). Aqueous potassium hydroxide (54 µL, 1.0M) was added and the reaction was stirred for 1 h. Tris buffer (2 mL, pH 8) was added and the solution was concentrated to almost dryness. The sample was prepared for Overhauser and ESR analysis by adding tris buffer until the total volume was 2 mL. ESR ($H_2O$, 0.16 mM, 200 G): singlet, linewidth 236 mG. Overhauser enhancement ($H_2O$, 0.159 mM) 130 at 32.4 mW microwave power.

EXAMPLE 19

Bis-(8-carboxy-2,2,6,6-tetramethylbenzo[1,2-d:4,5-d']-bis(1,3)-dioxol-4-yl)-mono-(8-carboxy-2,2,6,6-tetramethylbenzo[1,2-d:4,5-d']-bis(1,3)dithiol-4-yl) methanol

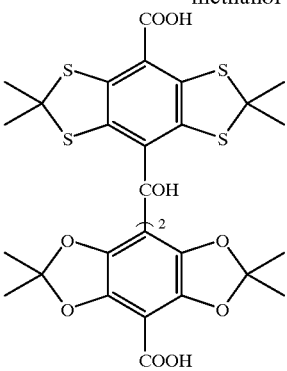

Dry TMEDA (1.21 mL, 8.04 mmol) and t-butyllithium (5.36 mL, 1.5M in pentane) were dissolved in dry cyclohexane (12 mL) at 0° C. Bis-(2,2,6,6-tetramethylbenzo[1,2-d:4,5-d']-bis(1,3)dioxol-4-yl)-mono-(2,2,6,6-tetramethylbenzo[1,2-d:4,5-d']-bis(1,3)dithiol-4-yl) methanol (0.608 g, 0.804 mmol) was then added at ambient temperature as a solid. After 20 min, solid carbon dioxide was added followed by dry ether (50 mL). After stirring for 17 h, the reaction mixture was filtered and the precipitate was dried. The acid was purified by preparative HPLC. Yield 0.285 g (40%).

$^1$H NMR ($CDCl_3$, 300 MHz) δ: 1.42–1.77 (m, 36H). $^{13}$C NMR ($CDCl_3$, 75 MHz) δ: 165.0, 140.3, 137.8, 136.1, 119.8, 118.1, 113.3, 100.2, 25.7.

EXAMPLE 20

Bis-(8-methoxycarbonyl-2,2,6,6-tetramethylbenzo[1,2-d:4,5-d']-bis(1,3)dioxol-4-yl)-mono-(8-methoxycarbonyl-2,2,6,6-tetramethylbenzo[1,2-d:4,5-d']-bis(1,3)dithiol-4-yl)methanol

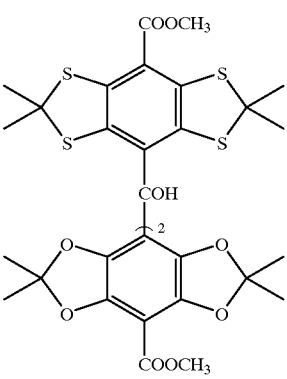

The tricarboxylic acid was prepared as described in Example 19, however, after treatment with carbon dioxide overnight, the reaction mixture was filtered and the precipitate was transferred to a reaction flask and mixed with potassium carbonate (0.222 g, 1.61 mmol) in DMF (15 mL). After stirring at ambient temperature for 30 min methyl iodide (0.228 g, 1.61 mmol) was added and the reaction was stirred overnight. To the mixture was added hydrochloric acid (45 mL, 0.25M) and ether (45 mL). The ether phase was separated and the aqueous phase was extracted with ether (2*70 mL). The collected organic phases were washed with slightly acidic water, (5*60 mL, 1 mL of 2M hydrochloric acid had been added), dried (Na$_2$SO$_4$) and evaporated. After preparative HPLC, 0.22 g (30%) of the pure ester was obtained.

$^1$H NMR (CDCl$_3$, 300 MHz) δ: 4.62 (s, 1H), 3.94 (s, 3H), 3.89 (s, 6H), 1.37–1.76 (m, 36H). $^{13}$C NMR (CDCl$_3$, 75 MHz) δ: 166.6, 163.5, 140.3, 137.8, 136.3, 120.0, 119.5, 118.2, 113.3, 99.8, 82.4, 52.2, 52.0, 25.8. MS (thermospray) m/z: 931 (M+).

EXAMPLE 21

Bis-(8-methoxycarbonyl-2,2,6,6-tetramethylbenzo[1,2-d:4,5-d']-bis(1,3)dioxol-4-yl)-mono-(8-methoxycarbonyl-2,2,6,6-tetramethylbenzo[1,2-d:4,5-d']-bis(1,3)dithiol-4-yl)methane

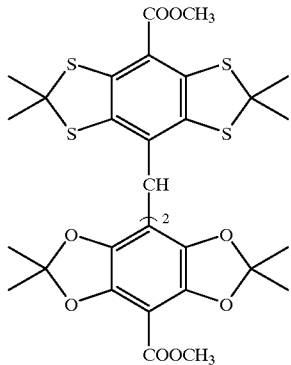

Bis-(8-methoxycarbonyl-2,2,6,6-tetramethylbenzo[1,2-d:4,5-d']-bis(1,3)dioxol-4-yl)-mono-(8-methoxycarbonyl-2,2,6,6-tetramethylbenzo[1,2-d:4,5-d']-bis(1,3)dithiol-4-yl) methanol (5 mg, 0.005 mmol) was dissolved in dry, degassed acetonitrile under an argon atmosphere. BF$_3$.Et$_2$O (2.0 μL, 0.011 mmol) and tin(II) chloride (3.0 mg, 0.016 mmol) were added. Amalgamated zinc (1.0 mg, 0.015 mmol), was added. The product was purified by flash chromatography (ether/heptane 5:1). Due to the small amount used the yield was not determined.

$^1$H NMR (CDCl$_3$, 300 MHz) δ: 5.33 (s, 1H), 3.92 (s, 6H), 3.25 (s, 3H), 1.16–1.37 (m, 36H). MS (thermospray) m/z: 914 (M+).

EXAMPLE 22

Bis-(8-methoxycarbonyl-2,2,6,6-tetramethylbenzo[1,2-d:4,5-d'-]bis(1,3)dioxol-4-yl)-mono-(8-methoxycarbonyl-2,2,6,6-tetramethylbenzo[1,2-d:4,5-d']-bis(1,3)dithiol-4-yl)methyl

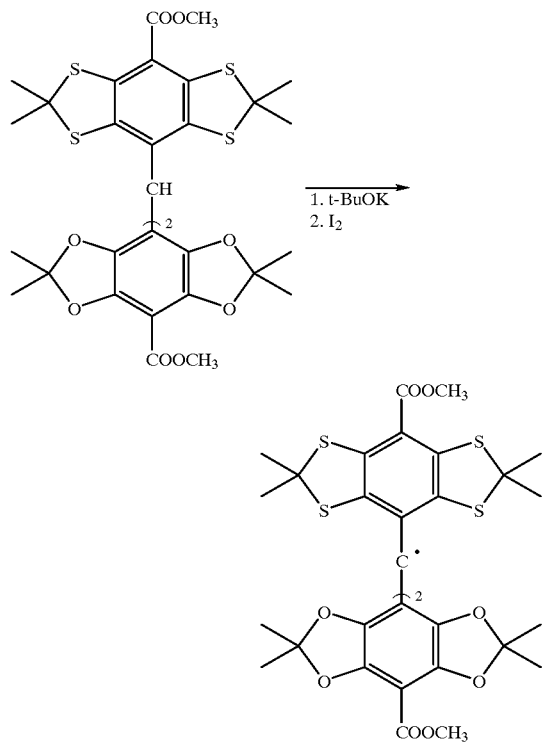

Procedure A:

Bis-(8-methoxycarbonyl-2,2,6,6-tetramethylbenzo-[1,2-d:4,5-d']-bis(1,3)dioxol-4-yl)-mono-(8-methoxycarbonyl-2,2,6,6-tetramethylbenzo[1,2-d:4,5-d']-bis(1,3)dithiol-4-yl) methane (5.0 mg, 0.5 mmol) was dissolved in a 1/1 mixture of dry, degassed DMSO and acetonitrile (1.0 mL) under argon atmosphere. Potassium t-butoxide (1.2 mg, 10.6 mmol) was added. The solution was added to a mixture of degassed ether (50 mL) and water (40 mL, pH 2).The ether layer was separated and evaporated. ESR (acetonitrile, 200 G) multiplet, linewidth 65 mG. Overhauser enhancement (acetonitrile): 38 at 1.1 W microwave power.

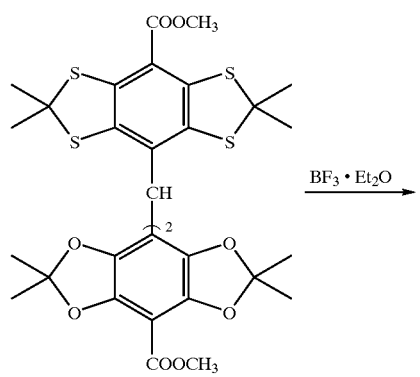

-continued

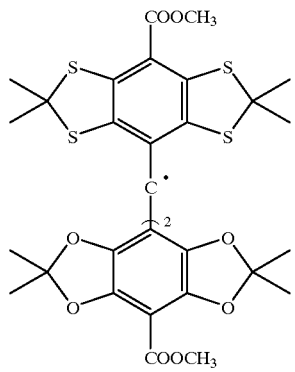

Procedure B:

Bis-(8-methoxycarbonyl-2,2,6,6-tetramethylbenzo[1,2-d:4,5-d']-bis(1,3)dioxol-4-yl)-mono-(8-methoxycarbonyl-2,2,6,6-tetramethylbenzo[1,2-d:4,5-d']-bis(1,3)dithiol-4-yl) methanol (30 mg, 0.032 mmol) was dissolved in dried and degassed acetonitrile (2.5 mL) in a dry and argon filled reaction vessel. $BF_3.Et_2O$ (13.0 μL, 0.064 mmol) was added. A sample from the reaction mixture showed a large Overhauser effect, thus a radical had been formed. The solution was transferred to separatory funnel containing degassed dichloromethane (25 mL) and water (70 mL). The dark green organic layer was separated, dried with $Na_2SO_4$ and evaporated. The yield was not determined. Overhauser enhancement (acetonitrile, 12.9 mM): 230 at 9 W microwave power.

EXAMPLE 23

Bis-(8-potassium carboxylate-2,2,6,6-tetramethylbenzo[1,2-d:4,5-d']-bis(1,3)dioxol-4-yl)-mono-(8-potassiumcarboxylate-2,2,6,6-tetramethylbenzo[1,2-d:4,5-d']-bis(1,3)dithiol-4-yl) methyl

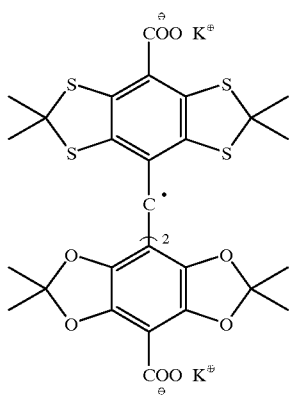

The radical was synthesized as described in Example 22B from bis-(8-carboxy-2,2,6,6-tetramethylbenzo[1,2-d:4,5-d']-bis(1,3)dioxol-4-yl)-mono-(8-carboxy-2,2,6,6-tetramethylbenzo[1,2-d:4,5-d']-bis(1,3)dithiole-4-yl) methanol (59.2 mg, 0.067 mmol) and $BF_3.Et_2O$ (26.0 μL, 0.13 mmol) in acetonitrile (2.0 mL) and dichloromethane (0.5 mL). The yield was not determined. ESR ($H_2O$, 200 G): singlet, linewidth 60 mG. Overhauser enhancement ($H_2O$, pH 9 buffer): 60 at 5 W microwave power.

EXAMPLE 24

2,2,6,6-Tetrakis-($^2H_3$-methyl)benzo[1,2-d:4,5-d']bis(1,3)dithiole

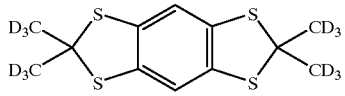

This compound was prepared from benzene-1,2,4,5-tetrathiole (20.0 g, 97 mmol), acetone-$d_6$ (48 mL, 0.65 mol) and $HBF_4$ (16.8 mL, 54% in ether, 0.123 mol) using the procedure described for the corresponding protio compound in WO-91/12024. Yield 20.9 g (72%).

$^1$H NMR ($CDCl_3$, 300 MHz) δ: 7.02 (s, 2H).

EXAMPLE 25

Tris-(2,2,6,6-tetrakis-($^2H_3$-methyl)-benzo[1,2-d:4,5-d']bis(1,3)dithiole)methanol

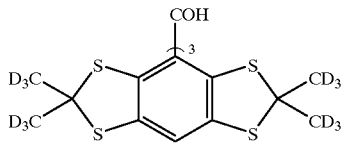

2,2,6,6-Tetrakis-($^2H_3$-methyl)-benzo[1,2-d:4,5-d']bis(1,3) dithiole (19.7 g, 66 mmol) was dissolved in dry diethyl ether (400 mL) under an atmosphere of argon. n-BuLi (41.2 mL, 1.6M in hexane) was added and the reaction mixture was stirred at ambient temperature for 2 h. Diethyl carbonate (2.40 mL, 19.8 mmol) was then added dropwise over a period of 30 minutes. After stirring overnight, ether (200 mL) and saturated aqueous $NaH_2PO_4$ (100 mL) were added. The organic phase was dried ($MgSO_4$) and evaporated and the residue was recrystallized from THF containing 5% acetonitrile. Yield: 10.8 g (53%).

$^1$H NMR ($CDCl_3$, 300 MHz) δ: 7.17 (s, 3H), 6.23 (s, OH, 1H). $^{13}$C NMR ($CDCl_3$, 75 MHz) δ: 138.8, 137.5, 136.8, 135.6, 133.1, 131.7, 126.6, 124.7, 116.4, 83.1, 64.5, 61.5, 35.2, 30.2, 29.5, 20.7, 12.3.

EXAMPLE 26

Tris-(8-ethoxycarbonyl-2,2,6,6-tetrakis-($^2H_3$-methyl)-benzo[1,2-d:4,5-d']bis(1,3)dithiole)methanol

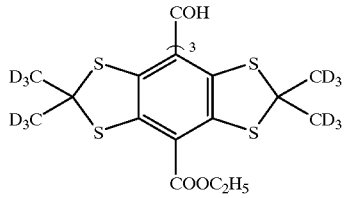

Tris-(2,2,6,6-tetrakis-($^2H_3$-methyl)-benzo[1,2-d:4,5-d'] bis(1,3)dithiole)methanol (10.8 g, 11.7 mmol) was dissolved in dry benzene (140 mL) together with TMEDA (17.6 mL, 118 mmol). t-BuLi (79 mL, 1.5M in pentane) was then added and the reaction mixture was stirred at ambient temperature for 35 min. The nearly homogeneous solution was then transferred into a solution of diethyl pyrocarbonate (90 mL, 611 mmol) in benzene (76 mL). After 2 h, a saturated aqueous solution of $NaH_2PO_4$ was added and the mixture was stirred for 10 min. The organic phase was dried ($MgSO_4$), evaporated and the product was recrystallized from acetonitrile. Yield: 5.30 g (40%).

$^1$H NMR ($CDCl_3$, 300 MHz) δ: 6.78 (s 1H, OH), 4.43 (m, 6H, $CH_2$), 1.46 (m, 9H, $CH_3$). $^{13}$C NMR ($CDCl_3$, 75 MHz) δ: 166.2, 141.8, 140.3, 139.2, 134.0, 121.3, 84.3, 62.3, 60.9, 60.8, 33.8, 31.8, 29.2, 28.6, 14.3.

EXAMPLE 27

Tris-(8-ethoxycarbonyl-2,2,6,6-tetrakis-($^2$H$_3$-methyl)-benzo[1,2-d:4,5-d']bis(1,3)dithiole)methyl

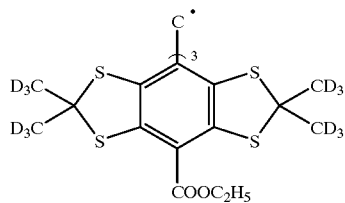

Tris-(8-ethoxycarbonyl-2,2,6,6-tetrakis-($^2$H$_3$-methyl)-benzo[1,2-d:4,5-d']bis(1,3)dithiole)methanol (5.33 g, 4.6 mmol) was dissolved in $CH_2Cl_2$ (40 mL) and a solution of trifluoromethane-sulfonic acid (1.5 mL, 17 mmol) in $CH_2Cl_2$ (5 mL) was then added. After stirring for 7 min, a solution of tin(II) chloride (1.74 g, 9.2 mmol) in THF (6 mL) was added and the mixture was stirred for another 10 min. A saturated aqueous solution of $NaH_2PO_4$ was added and, after stirring for a few minutes, the organic phase was separated, dried ($MgSO_4$) and evaporated. The radical was not purified, HPLC indicated 80% pure product. Yield: 4.72 g (91%). ESR (diethyl ether, 200 G): singlet, linewidth 180 mG. Overhauser enhancement (diethyl ether): 192 at 5 W microwave power. Stability measurements: Half life in acetonitrile without exclusion of air: >30000 h.

EXAMPLE 28

Tris-(8-carboxyl-2,2,6,6-tetrakis-($^2$H$_3$-methyl)-benzo[1,2-d:4,5-d']bis(1,3)dithiole)methyl Sodium Salt

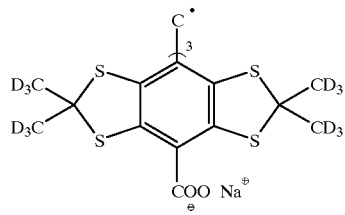

Tris-(8-ethoxycarbonyl-2,2,6,6-tetrakis-($^2$H$_3$-methyl)-benzo[1,2-d:4,5-d']bis(1,3)dithiole)methyl (4.72 g, 4.21 mmol) was dissolved in dioxane (82 mL) and 1M KOH (41 mL) was added. The solution was stirred at 50° C. for 2 h and then evaporated. Water (50 mL) was added and stirring was continued at 50° C. for another hour. The aqueous solution was acidified with 2M HCl and extracted with ether (2*150 mL). The organic phases were dried ($MgSO_4$) and evaporated. The product was purified by preparative HPLC. The combined fractions were then concentrated and partitioned between diethyl ether and water. The organic phase was extracted with water and a sufficient amount of aqueous 1M NaOH for the product to dissolve in the aqueous phase. After lyophilization, 3.5 g (80%) of the pure radical was obtained. ESR (0.94 mM in $H_2O$ buffered to pH 7, 200 G): singlet, linewidth 74 mG. Overhauser enhancement (aqueous solution as above): 71 at 5 W microwave power. Stability measurements: Half life in water without exclusion of air: 5400 h.

EXAMPLE 29

1,3-Dihydroxypropane-2-one 1,3-diacetate

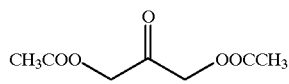

1,2-dihydroxypropane-2-one 1,3-diacetate was prepared using the procedure described in the literature (Bentley and McCrae Org. Chem. 35 2082 (1970)). 1,3-Dihydroxyacetone (60 g) was dissolved in pyridine (200 mL). The solution was cooled to 0° C., acetic anhydride (200 mL) was added and the reaction mixture was stirred at ambient temperature for 2 h. The pyridine, acetic acid and acetic anhydride were evaporated in vacuum. The residue was dissolved in ethyl acetate (400 mL), washed with 1M HCl (2*100 mL) and water (100 mL). The solution was dried ($Na_2SO_4$) and evaporated. The crude product was recrystallized from ligroin. Yield: 63 g (56%).

$^1$H NMR ($CDCl_3$, 300 MHz) δ: 4.75 (s, 4H, $CH_2$), 2.17 (s, 6H, $CH_3$)

EXAMPLE 30

2,2,6,6-Tetra(acetoxymethyl)benzo[1,2-d:4,5-d']bis(1,3)dithiole

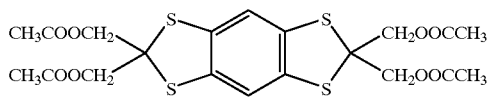

The reaction was performed under argon atmosphere using deoxygenated solvents. 1,2,4,5-Benzotetrathiole (4.9 g, 24 mmol) and 1,3-dihydroxypropane-2-one 1,3-diacetate (10.4 g, 60 mmol) were mixed in toluene (250 mL). The mixture. was cooled to 0° C. and $HBF_1$ (10.7 mL, 54% in diethyl ether) was added and the reaction mixture was stirred at 0° C. for 2 h. The organic solution was decanted and the residue was extracted with toluene (3*50 mL). The combined organic phases were evaporated and the crude product was purified by chromatography (neutral alumina, ethyl acetate:heptane 1:1). Yield: 3.5 g (28%).

$^1$H NMR ($CDCl_3$, 300 MHz) δ: 6.93 (s, 2H, ArH), 4.50 (s, 8H, CH2), 2.09 (s, 12H, CH3).

EXAMPLE 31

2,2,6,6-Tetra(hydroxymethyl)benzo[1,2-d:4,5-d']bis(1,3)dithiole

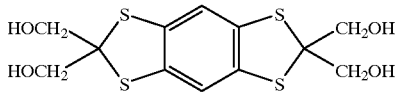

2,2,6,6-Tetra(acetoxymethyl)benzo[1,2-d:4,5-d']bis(1,3)dithiole (1.8 g, 3.5 mmol) and $K_2CO_3$ (1.9 g) were stirred in methanol (100 mL) for 1 h at ambient temperature. The solvent was evaporated and water (100 mL) was added. The mixture was neutralized (2M HCl) and the precipitate was collected. Yield: 1.20 g (99%).

$^1$H NMR (DMSO-$d_6$, 300 MHz) δ: 7.09 (s, 2H, ArH), 5.55 (t, 4H, J 5.6 Hz, OH), 3.74 (d, 8H, J 5.6 Hz, $CH_2$). 13C NMR (DMSO-$d_6$, 75 MHz) δ: 134.4, 116.5, 75.7, 63.8.

EXAMPLE 32

2,2,6,6-Tetra(dimetylthexylsilyloxymethyl)benzo[1,2-d:4,5-d']bis(1,3)dithiole

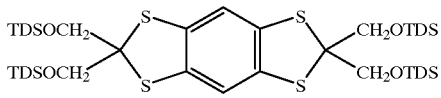

The reaction was performed under argon atmosphere. 2,2,6,6-Tetra(hydroxymethyl)benzo[1,2-d:4,5-d']bis(1,3)dithiole (0.8 g, 2.2 mmol) was dissolved in DMF (20 mL). Imidazole (1.1 g, 15.8 mmol) was added and the solution was cooled to 0° C. Dimethylthexylsilyl chloride (2.8 g, 15.8 mmol) was added dropwise (ca 2 min). The solution was stirred for 48 hours at ambient temperature. The reaction mixture was poured into ice/water, $CH_2Cl_2$ (100 mL) was added and the two phases were separated. The organic phase was washed with 1M HCl and water (3*100 mL). The solution was dried ($Na_2SO_4$) and evaporated. The product was purified by column chromatography using dichloromethane-heptane (1:9) as eluent. Yield: 1.1 g (52%).

$^1$NMR (CDCl$_3$, 300 MHz) δ: 6.84 (s, 2H, ArH), 3.94 (s, 8H, CH$_2$), 1.62 (septet, 4H, J 6.8 Hz, CH), 0.88 (d, 24H, J 6.8 Hz, CH$_3$), 0.84 (s, 24H, CH$_3$), 0.08 (s, 24H, Si(CH$_3$)$_2$). $^{13}$C NMR (CDCl$_3$, 75 MHz) δ: 134.3, 115.8, 74.2, 65.0, 34.2, 25.1, 20.3, 18.6, −3.6.

EXAMPLE 33

Bis(2,2,6,6-tetra(dimetylthexylsilyloxymethyl)benzo[1,2-d:4,5-d']bis(1,3)dithiol-4-yl)-mono(2,2,6,6-tetramethylbenzo[1,2-d:4,5-d']-bis(1,3)dioxol-4-yl))methanol

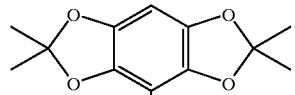

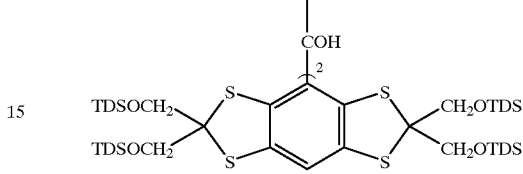

The reaction was performed under argon atmosphere. 2,2,6,6-Tetra(dimetylthexylsilyloxymethyl)benzo[1,2-d:4,5-d']bis(1,3)dithiole (7.0 g, 7.6 mmol) was dissolved in dry THF (50 mL). The solution was cooled to −70° C. n-Butyllithium (5.0 mL, 1.6M in hexane) was added and the temperature was allowed to attain ambient temperature and was stirred for 1 h. The solvent was evaporated in vacuum at ambient temperature and diethyl ether (20 mL) was added. Then, 4-ethoxycarbonyl-2,2,6,6-tetramethylbenzo[1,2-d:4,5-d']-bis(1,3)dioxole (0.8 g, 2.9 mmol) was added in one portion and the reaction mixture was stirred at ambient temperature for 12 h. The mixture was poured into a $NaH_2PO_4$ solution, the phases were separated and the aqueous phase was extracted with diethyl ether (2*100 mL). The organic phases were dried ($Na_2SO_4$) and evaporated. The residue was purified by preparative HPLC. Yield: 3.7 g (62%).

$^1$H NMR (CDCl$_3$, 300 MHz) δ: 6.80 (s, 2H, ArH), 6.26 (s, 1H, ArH), 4.95 (s, 1H, OH), 3.8 (br m, 16H, CH$_2$), 1.5 (br m, 20H, CH$_3$+CH), 0.9 (d, 48H, CH$_3$), 0.7 (s, 48H, CH$_3$), 0.2 (2 s, 48H, Si(CH3)$_2$). $^{13}$C NMR (CDCl$_3$, 75 MHz) δ: 141.5, 140.3, 139.8, 139.6, 131.7, 118.6, 117.1, 108.1, 94.4, 80.0, 65.4, 34.1, 25.9, 25.0, 20.3, 18.7, −3.2.

EXAMPLE 34

Bis(8-ethoxycarbonyl-2,2,6,6-tetra(hydroxymethyl)benzo[1,2-d:4,5-d']bis(1,3)dithiol-4-yl)-mono(8-ethoxycarbonyl-2,2,6,6-tetramethylbenzo[1,2-d:4,5-d']-bis(1,3)dioxol-4-yl))methanol

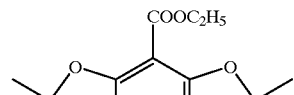

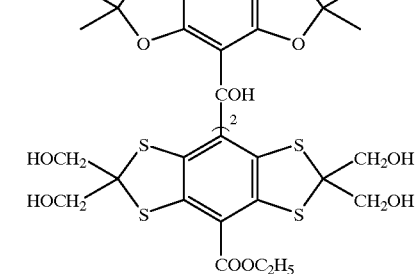

Bis(2,2,6,6-tetra(dimetylthexylsilyloxymethyl)benzo[1,2-d:4,5-d']bis(1,3)dithiol-4-yl)-mono(2,2,6,6- tetramethylbenzo[1,2-d:4,5-d']-bis(1,3)dioxol-4-yl))methanol (3.2 g, 1.54 mmol) was dissolved in heptane (12.8 mL) and dry benzene (10.7 mL) together with TMEDA (3.2 mL, 21.6 mmol) under an atmosphere of argon. The solution was cooled to −22° C. and t-BuLi (14.4 mL, 1.5M in pentane) was added. After stirring for 3 h at −22° C., the reaction mixture was transferred into a solution of diethyl pyrocarbonate (12.8 mL, 87 mmol) in heptane (23 mL) and dry benzene (23 mL) which was kept at −22° C. The reaction mixture was then allowed to attain ambient temperature. After stirring for an additional hour, a saturated aqueous solution of NaH$_2$PO$_4$ (40 mL) was added. The mixture was stirred for one hour, the organic phase was separated, washed with water (2*100 mL) and acetonitrile (2*100 mL). The heptane/benzene phase was evaporated and then dissolved in THF (25 mL). A solution of Bu$_4$NF in THF (20 mL, 20 mmol) was added and the mixture was stirred overnight. After evaporation of the solvent, the residue was partitioned between water (300 mL) and ethyl acetate (300 mL). The organic phase was washed with water (2*100 mL), dried (Na$_2$SO$_4$) and evaporated. Purification by preparative HPLC gave 400 mg (22%) pure product.

$^1$H NMR (CDCl$_3$, 300 MHz) δ: 5.78–5.92 (m, 6H), 5.03–5.52 (m, 24H), 2.98–3.21 (m, 12H), 2.90 (t, 6H, J 7.0 Hz), 2.84 (t, 3H, J 6.9 Hz).

EXAMPLE 35

Bis(8-ethoxycarbonyl-2,2,6,6-tetra(hydroxymethyl)benzo[1,2-d:4,5-d']bis(1,3)dithiol-4-yl)-mono(8-ethoxycarbonyl-2,2,6,6-tetramethylbenzo[1,2-d:4,5-d']-bis(1,3)dioxol-4-yl))methyl

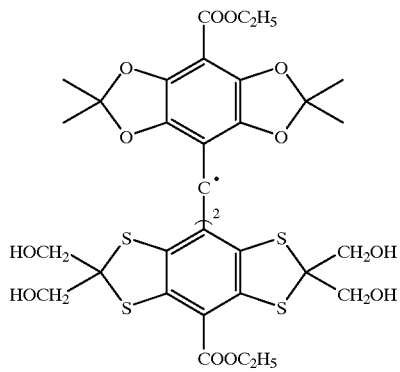

Bis(8-ethoxycarbonyl-2,2,6,6-tetra(hydroxymethyl)benzo[1,2-d:4,5-d']bis(1,3)dithiol-4-yl)-mono(8-ethoxycarbonyl-2,2,6,6-tetramethylbenzo[1,2-d:4,5-d']-bis(1,3)dioxol-4-yl))methanol (294 mg, 0.25 mmol) was dissolved in acetonitrile (70 mL) under an atmosphere of argon. After cooling to 0° C., trifluoromethane sulfonic acid (190 μL, 2.2 mmol) was added. After stirring for 3 min, tin(II) chloride (48 mg, 0.25 mmol) dissolved in acetonitrile (7 mL) was added. After 1 min, a saturated aqueous solution of NaH$_2$PO$_4$ (50 mL) was added. The aqueous phase was washed with acetonitrile (2*50 mL), the combined organic phases were dried (Na$_2$SO$_4$) and evaporated. Purification by preparative HPLC gave 176 mg (61%) of the pure product. ESR (H$_2$O, 200 G): singlet, linewidth 433 mG.

EXAMPLE 36

Bis(8-carboxy-2,2,6,6-tetra(hydroxymethyl)benzo[1,2-d:4,5-d']bis(1,3)dithiol-4-yl)-mono(8-carboxy-2,2,6,6-tetramethylbenzo[1,2-d:4,5-d']-bis(1,3)dioxol-4-yl))methyl Sodium Salt

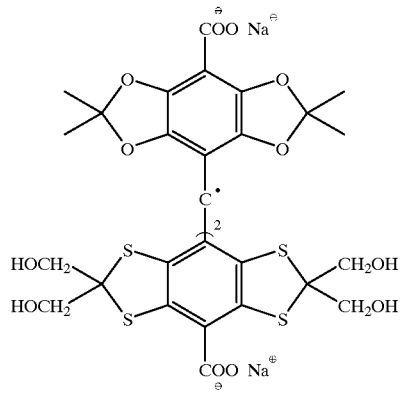

Bis(8-ethoxycarbonyl-2,2,6,6-tetra(hydroxymethyl)benzo[1,2-d:4,5-d']bis(1,3)dithiol-4-yl)-mono(8-ethoxycarbonyl-2,2,6,6-tetramethylbenzo[1,2-d:4,5-d']-bis(1,3)dioxol-4-yl))methyl (316 mg, 0.275 mmol) was dissolved in a mixture of 1M aqueous NaOH (3 mL), water (1.5 mL) and ethanol (3 mL). The solution was stirred at ambient temperature for 15 min, the ethanol was removed by evaporation, and the residue was stirred at ambient temperature for additional 2 hours. After evaporation to near dryness, the pure acid (240 mg, 82%) was isolated by preparative HPLC followed by lyophilization. The acid was converted into the corresponding sodium salt by the addition of water (50 mL) followed by adjustment of the pH to 7 with 1M aqueous NaOH and lyophilization. ESR (3.4 mM in H$_2$O, 200 G): singlet, linewidth 120 mG. Overhauser enhancement (aqueous solution as above): 164 at 5 W microwave power. Stability measurements: Half life in water without exclusion of air: 120 h.

EXAMPLE 37

2,2,6,6-Tetramethylbenzo[1,2-d:5,4-d']bis(1,3)oxathiole

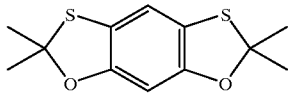

2,6-Dioxo-benzo[1,2-d:5,4-d']bis(1,3)oxathiole (1.0 g, 4.4 mmol), prepared according to the literature procedure (Fiedler, H. Berichte 95, 1771 (1962)) was suspended in dry methanol (30 mL) and a solution of sodium methoxide in methanol (prepared from 20 mL methanol and 2.2 mmol sodium) was then added over a period of 15 minutes. After stirring for 15 minutes, the mixture was poured onto diethyl ether (50 mL) and 1M aqueous HCl (25 mL). The aqueous phase was extracted twice with ether and the combined organic phases were dried (MgSO$_4$) and evaporated. The residue (0.60 g) was dissolved in dry acetonitrile (40 mL) containing acetone (6 mL) and BF$_3$.Et$_2$O (4 mL) was then added. After stirring for 20 minutes, water (100 mL) and

EXAMPLE 38

8-Trimethylsilyl-2,2,6,6-tetramethylbenzo[1,2-d:5,4-d']-bis(1,3)oxathiole

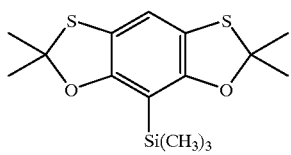

The reaction was performed under an argon atmosphere using deoxygenated solvents. 2,2,6,6-tetramethylbenzo[1,2-d:5,4-d']-bis(1,3)oxathiole (6.0 g, 23.6 mmol) was dissolved in dry THF (120 mL). The mixture was cooled on an ice-bath and n-butyllithium (10.8 mL, 2.5M in hexane) was added dropwise over 10 min. After 15 min, chlorotrimethylsilane (6.0 mL, 47.2 mmol) was added dropwise over 5 min. After another 15 min, the reaction mixture was quenched with dietyl ether/aq. NaHCO$_3$, the aqueous layer was extracted with ether and the combined organic layers were washed with water and dried (Na$_2$SO$_4$). After evaporation and chromatography (silica gel, chloroform) essentially pure product (6.3 g, 92%) could be collected.

$^1$H NMR (CDCl$_3$, 300 MHz) δ: 6.80 (s, 1H, ArH), 1.79 (s, 12H, CH3), 0.28 (s, 9H, SiCH3).

EXAMPLE 39

Tris-(8-trimethylsilyl-2,2,6,6-tetramethylbenzo[1,2-d:5,4-d']-bis(1,3)oxathiol-4-yl)methanol

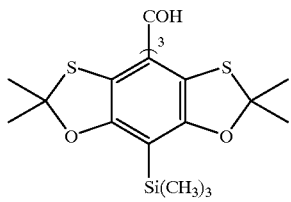

The reaction was performed under an argon atmosphere using deoxygenated solvents. 8-Trimethylsilyl-2,2,6,6-tetramethyl-benzo[1,2-d:5,4-d']-bis(1,3)oxathiole (14.2 g, 43.5 mmol) was dissolved in dry THF (300 mL). The mixture was cooled using to −70° C. and n-butyllithium (59.0 mmol, 2.5M in hexane) was added dropwise over 10 min and the mixture was then left to attain ambient temperature over 90 min. Neat diethyl carbonate (1.75 mL, 14.5 mmol) was added dropwise over 60 min and the mixture was then stirred overnight. The reaction mixture was then quenched with diethyl ether/aq. NaH$_2$PO$_4$, the aqueous layer was extracted with ether and the combined organic layers were washed twice with water, dried (Na$_2$SO$_4$), evaporated, chromatographed (silica gel; dichloro-methane:heptane 1:2) and finally triturated with ethanol to give the pure product as colorless crystals. Yield: 8.4 g (58%).

$^1$H NMR (CDCl$_3$, 300 MHz) δ: 4.43 (s, 1H, OH), 1.78–1.55 (m, 36H, CH$_3$), 0.28 (s, 27H, SiCH$_3$). 13C NMR (CDCl$_3$, 75 MHz) δ: 158.8, 128.5, 120.7, 119.5, 116.1, 105.7, 95.6, 94.3, 81.5, 30.9, 30.5, 29.1, 28.9, 0.5. MS (electrospray) m/z: 1005 (M+H).

EXAMPLE 40

Tris-(2,2,6,6-tetramethylbenzo[1,2-d:5,4-d']-bis(1,3) oxathiol-4-yl)methanol

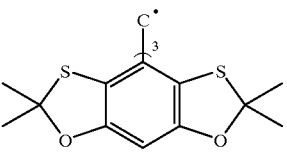

Tris-(8-trimethylsilyl-2,2,6,6-tetramethylbenzo[1,2-d:5,4-d']-bis(1,3)oxathiol-4-yl)methanol (0.62 g, 0.62 mmol) was dissolved in acetonitrile (150 mL). Sodium iodide (0.75 g, 6.0 mmol) and chlorotrimethylsilane (0.65 g, 6.0 mmol) was added in one portion. The mixture was stirred for 20 min and then poured onto diethyl ether/aq. NaHCO$_3$. The aqueous layer was extracted with ether and the combined organic layers were washed twice with water, dried (Na$_2$SO$_4$), evaporated, chromatographed (silica gel; dichloromethane) and finally triturated with ethyl acetate to yield the product as slightly brown crystals. Yield: 0.44 g (87%).

$^1$H NMR (CDCl$_3$, 300 MHz) δ: 6.42 (s, 3H, ArH), 4.59 (s, 1H, OH), 1.82–1.62 (m, 36H, CH3). 13C NMR (CDCl$_3$, 75 MHz) δ 154.4, 154.3, 127.1, 121.2, 120.4, 97.1, 96.6, 96.0, 81.1, 30.9, 30.4, 29.1 MS (electrospray) m/z: 788 (M+).

EXAMPLE 41

Tris-(8-ethoxycarbonyl-2,2,6,6-tetramethylbenzo[1,2-d:5,4-yl)methanol

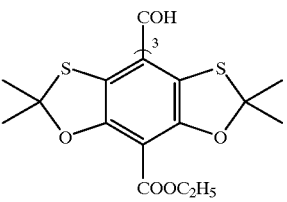

The reaction was performed under an argon atmosphere using deoxygenated solvents. Tris-(2,2,6,6-tetramethylbenzo 1,2-d:5,4-d']bis(1,3)-oxathiol-4-yl) methanol (0.40 g, 0.50 mmol) was suspended in dry diethyl ether (80 mL). The mixture was stirred and n-butyllithium (1.5 mL, 2.5M in hexane) was added dropwise over 10 min. After 10 min, the temperature was lowered to −78° C. and neat diethyl carbonate (5.25 g, 44.5 mmol) was added in one portion. After 10 min, the cooling bath was removed and after 90 min the reaction mixture was poured onto diethyl ether/aq. NaH$_2$PO$_4$. The aqueous layer was extracted with ether and the combined organic layers were washed twice with water, dried (Na$_2$SO$_4$) and evaporated. The resulting yellow solid was purified by preparative HPLC. Yield: 0.20 g (39%).

$^1$H NMR (CDCl$_3$, 300 MHz) δ: 4.76 (S, 1H, OH), 4.86 (dq, 6H, CH2), 1.85–1.65 (m, 36H, CH$_3$), 1.37 (s, 6H, CH$_3$) MS (electrospray) m/z: 1004 (M+).

EXAMPLE 42

Tris-(8-ethoxycarbonyl-2,2,6,6-tetramethylbenzo[1,2-d:5,4-d']-bis(1,3)oxathiol-4-yl)methyl

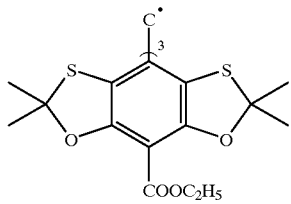

The reaction was performed under an argon atmosphere using deoxygenated solvents. Tris-(8-ethoxycarbonyl-2,2,6,6-tetramethyl-benzo[1,2-d:5,4-d']-bis(1,3)oxathiol-4-yl) methanol (0.10 g, 0.10 mmol) was dissolved in dichloromethane (20 mL) and stirred with $BF_3.Et_2O$ (0.10 mL, 0.80 mmol) for 48 min. A solution of tin(II) chloride (32 mg, 0.17 mmol) in THF (4 mL) was added and after 3 min, the mixture was poured onto water/dichloromethane. The organic layer was dried ($Na_2SO_4$) and evaporated. Purification by preparative HPLC gave the pure radical. Yield: 50 mg (50%). ESR (diethyl ether, 200 G): 9 equidistant lines, $a_H$=85 mG, linewidth 40 mG. Stability measurements: Half life in acetonitrile without exclusion of air: 5800 h.

EXAMPLE 43

Tris-(8-ethoxycarbonyl-3,3,5,5-tetraoxo-2,2,6,6-tetramethyl-benzo[1,2-d:5,4-d']-bis(1,3)oxathiol-4-yl)methyl

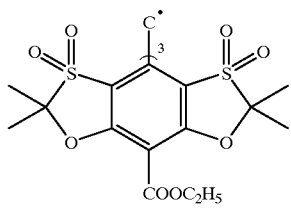

Tris-(8-ethoxycarbonyl-2,2,6,6-tetramethylbenzo[1,2-d:5,4-d']-bis(1,3)oxathiol-4-yl)methyl (0.050 g, 0.050 mmol) was dissolved in a premixed solution of trifluoroacetic acid (3 mL), acetic acid (3 mL), acetic anhydride (3 mL) and $H_2O_2$ (1 mL, 35% aqueous solution) and was left under an argon atmosphere for 80 h. The mixture was poured onto a saturated aqueous solution of NaCl and dichloromethane. The organic layer was washed with sat. NaCl and evaporated. After preparative HPLC, 0.008 g (16%) of the pure radical was isolated. MS (electrospray) m/z: 1202 (M+Na)+, 1180 (M+H)+. ESR: (H20, 200 G): singlet, linewidth 120 mG. Overhauser enhancement ($H_2O$): 221 with 10 W microwave power. Stability measurements: Half life in acetonitrile without exclusion of air: 800 h.

EXAMPLE 44

Tris-(8-carboxy-2,2,6,6-tetramethylbenzo-[1,2-d:5,4-d']-bis-(1,3)oxathiol-4-yl)methanol

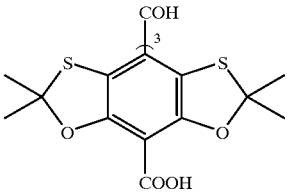

The reaction was performed under an argon atmosphere using deoxygenated solvents. Tris-(2,2,6,6-tetramethylbenzo[1,2-d:5,4-d']bis(1,3)-oxathiol-4-yl) methanol (5.45 g, 53.5 mmol) was suspended in dry diethyl ether (800 mL). The mixture was stirred and n-butyllithium (33.5 mL, 2.5M in hexane) was added dropwise over 10 min. After 1 hour, the temperature was lowered to −78° C. and the mixture was rapidly transferred to a flask containing a large excess of solid carbon dioxide. The mixture was allowed to reach ambient temperature and was then poured onto water. The organic layer was removed and discarded and the aqueous layer acidified (pH 0) and extracted three times with ether. The combined organic layers were dried ($Na_2SO_4$) and evaporated. The resulting yellow solid was purified by preparative HPLC. Yield: 2.6 g (42%)

$^1$H NMR (DMF-$d_6$, 300 MHz) δ: 4.71 (s, 1H, OH), 1.85–1.69 (m, 36H, $CH_3$). $^{13}$C NMR (DMF-$d_6$, 75 MHz) δ: 205.3, 152.1, 122.0, 121.4, 105.5, 98.0, 97.2, 81.0, 30.5, 29.8, 28.3, 28.2. MS (electrospray) m/z: 943 (M+Na).

EXAMPLE 45

Tris-(8-chlorocarbonyl-2,2,6,6-tetramethylbenzo[1,2-d:5,4-d']-bis(1,3)oxathiol-4-yl)methanol

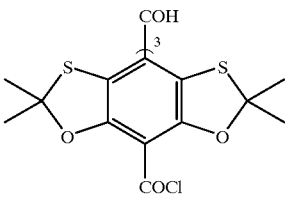

Tris-(8-carboxy-2,2,6,6-tetramethylbenzo-[1,2-d:5,4-d']-bis-(1,3)oxathiol-4-yl)methanol (0.92 g, 1.0 mmol) was dissolved in thionyl chloride (8 mL) and one drop of dimethylformamide was added. After 1 h, the mixture was placed on a rotary evaporator and evaporated with benzene (5*10 mL). A close to quantitative yield of orange crystals, which were not further purified, was obtained.

$^1$H NMR ($CDCl_3$, 300 MHz) δ: 4.70 (s, 1H, OH), 1.86–1.67 (m, 36H, $CH_3$). $^{13}$C NMR ($CDCl_3$, 75 MHz) δ: 162.3, 151.4, 151.3, 122.1, 122.0, 109.0, 99.5, 98.5, 81.0, 31.0, 30.5, 29.2, 29.1.

EXAMPLE 46

Tris-((8-(2,2-dimethyl-1,3-dioxiran-4-yl)-carbonyl)-2,2,6,6-tetramethylbenzo[1,2-d:5,4-d']-bis(1,3)oxathiol-4-yl)methanol

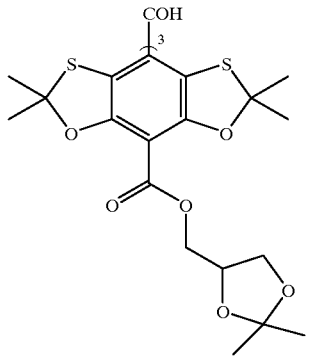

400 mg Sodium was stirred with 1,2-O-isopropylideneglycerine (5 mL) for 2 h. The resulting mixture, containing a large excess of the Na-alcoholate, was decanted from unreacted sodium and mixed with a solution of tris-(8-chlorocarbonyl-2,2,6,6-tetramethyl-benzo[1,2-d:5,4-d']-bis(1,3)oxathiole-4-yl)methanol (0.10 g, 0.10 mmol) in 1,2-O-isopropylideneglycerine (5 mL). After stirring for 5 h, the mixture was poured onto dichloromethane/water and the organic layer was dried ($Na_2SO_4$) and evaporated. Purification by preparative HPLC gave the triester as a slightly yellow solid.

$^1$H NMR ($CDCl_3$, 300 MHz) δ: 4.79 (s, 1H), 4.42–3.90 (m, 15H) 1.85–1.65 (m, 36H), 1.56–1.38 (m, 18H). MS (electrospray) m/z: 1285 (M+Na).

EXAMPLE 47

Tris-((8-(2,3-dihydroxy-1-propyl)-carbonyl)-2,2,6,6-tetra-methylbenzo[1,2-d:5,4-d']-bis(1,3)oxathiol-4-yl)methanol

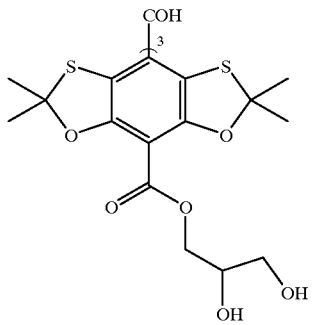

A solution of sodium 1,2-O-isopropylidenglyceride (prepared from 0.28 g of sodium and 1,2-O-isopropylidenglycerine (5 mL) as described in Example 46) was stirred overnight with a solution of tris-(8-chlorocarbonyl-2,2,6,6-tetramethyl-benzo[1,2-d:5,4-d']-bis(1,3)oxathiol-4-yl)methanol (0.88 g, 0.88 mmol) in 1,2-O-isopropylideneglycerine (5 mL), and the resulting crude ketal was stirred with acetonitrile (100 mL) mixed with conc. HCl (25 mL). After 2 h, the mixture was transferred to a separatory funnel and the two layers were separated. Both layers were partitioned between dichlorometane/water three times respectively. The aqueous layers were discarded and the combined organic layers were dried ($Na_2SO_4$) and evaporated. Purification by preparative HPLC yielded 0.75 g (75%) of the pure triester.

$^1$H NMR ($CDCl_3$, 300 MHz) δ: 4.85 (s, 1H), 4.54–3.70 (m, 17H)1.85–1.65 (m, 36H). MS (electrospray) m/z: 1143 (M+Na).

EXAMPLE 48

Tris-((8-(2,3-dihydroxy-1-propyloxy)-carbonyl)-2,2,6,6-tetra-methylbenzo[1,2-d:5,4-d']-bis(1,3)oxathiol-4-yl)methyl

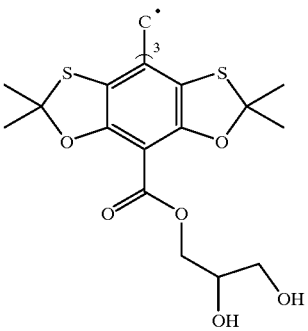

The reaction was performed under an argon atmosphere using deoxygenated solvents. Tris-((8-(2,3-dihydroxy-1-propyl)-2,2,6,6-tetramethylbenzo[1,2-d:5,4-d']-bis(1,3)oxathiole-4-yl)methanol (0.053 g, 0.046 mmol) was dissolved in dichloromethane (6 mL) and stirred with $BF_3.Et_2O$ (0.053 mL, 0.42 mmol) for 10 min. A solution of tin(II) chloride (25 mg, 0.13 mmol) in THF (2 mL) was added and after 10 min, the mixture was poured onto water/dichloromethane. The organic layer was dried ($Na_2SO_4$) and evaporated. Purification by preparative HPLC yielded 22 mg (42%) of the pure radical. MS (electrospray) m/z: 1142 (M+H). ESR ($H_2O$, 200 G): singlet, linewidth 300 mG. Overhauser enhancement ($H_2O$): 56 at 10 W microwave power. Stability measurements: Half life in acetonitrile:water (1:1)without exclusion of air: 250 h.

EXAMPLE 49

Tris-(8-di-(2-hydroxyethyl)aminocarbonyl-2,2,6,6-tetramethylbenzo[1,2-d:5,4-d']-bis(1,3)oxathiol-4-yl)methanol

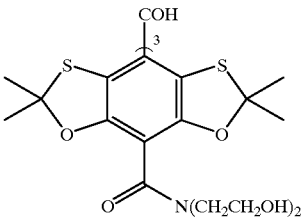

Tris-(8-chlorocarbonyl-2,2,6,6-tetramethyl-benzo[1,2-d:5,4-d']-bis(1,3)oxathiol-4-yl)methanol (0.80 g, 0.80 mmol) was dissolved in benzene (200 mL). A solution of of bis(2-hydroxyethyl)amine (8.0 g, 48 mmol) in water (200 mL) was added and after vigorous stirring overnight, the mixture was transferred to a separatory funnel. The aqueous layer was removed and the remaining solid plus the benzene layer was evaporated, dissolved in methanol and passed through a short column (neutral alumina). After elution of unwanted materials with acetonitrile, the amide was eluted with methanol. After evaporation, the product was stirred with water (50 mL) at 40° C. for 2 h and then isolated by filtration. After drying, 0.60 g (60%) of the pure amide was obtained.

$^1$H NMR ((CD$_3$)$_2$CO, 300 MHz) δ: 3.80–2.80 (m, 16H), 1.85–1.65 (m, 36H). MS (electrospray) m/z: 1182 (M+H).

EXAMPLE 50

Tris-(8-di-(2-hydroxyethyl)aminocarbonyl-2,2,6,6-tetramethylbenzo[1,2-d:5,4-d']-bis(1,3)oxathiol-4-yl) methyl

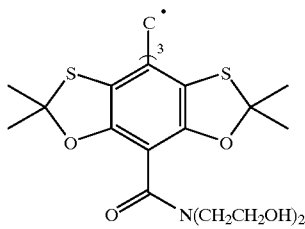

The reaction was performed under an argon atmosphere using deoxygenated solvents. Tris-(8-di-(2-hydroxyethyl) amino-carbonyl-2,2,6,6-tetramethylbenzo[1,2-d:5,4-d']-bis (1,3)oxathiol-4-yl)methanol (0.032 g, 0.027 mmol) was dissolved in dichloromethane (40 mL) and BF$_3$.Et$_2$O (0.15 mL, 1.19 mmol) was added. After stirring for 20 min, a solution of 15 mg SnCl$_2$ (15 mg, 0.079 mmol) in THF (10 mL) was added. After stirring for an additional 5 min, the mixture was poured onto sat. NaCl/dichloromethane. The organic layer was dried (Na$_2$SO$_4$) and evaporated. Purification by preparative HPLC yielded 22 mg (69%) of the pure radical. ESR (H$_2$O, 200 G): singlet, linewidth 600 mG. Overhauser enhancement (H$_2$O): 124 at 10 W microwave power. MS (electrospray) m/z: 1164 (M$^+$).

EXAMPLE 51

Tris-(8-dimethylaminocarbonyl)-2,2,6,6-tetramethylbenzo[1,2-d:5,4-d']-bis(1,3)oxathiol-4-yl) methanol

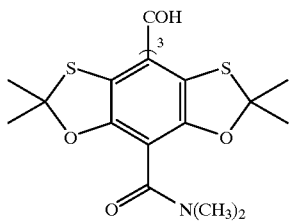

Tris-(8-chlorocarbonyl-2,2,6,6-tetramethyl-benzo[1,2-d:5,4-d']-bis(1,3)oxathiol-4-yl)methanol (0.50 g, 0.50 mmol) was dissolved in benzene (20 mL). A solution of of dimethylamine (3.0 g, 67 mmol) in water (20 mL) was added and after treatment with ultrasound for 1 h, the mixture was transferred to a separatory funnel. The aqueous layer was extracted with benzene and the combined organic layers were dried (Na$_2$SO$_4$) and evaporated. Yield: 0.52 g (100%).

$^1$H NMR ( (CD$_3$)$_2$CO, 300 MHz) δ: 4.63 (s, 1H, OH), 3.10–2.90 (m, 18H, NCH$_3$) 1.81–1.61 (m, 36H, CH$_3$).

EXAMPLE 52

Tris-(8-dimethylaminocarbonyl-2,2,6,6-tetra-methylbenzo[1,2-d:5,4-d']-bis(1,3)oxathiol-4-yl) methyl

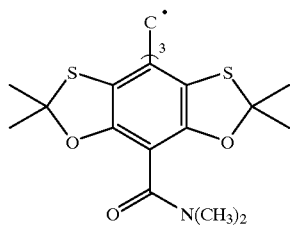

The reaction was performed under an argon atmosphere using deoxygenated solvents. Tris-(8-dimethylaminocarbonyl-2,2,6,6-tetramethylbenzo[1,2-d:5, 4-d']-bis(1,3)oxathiol-4-yl)methanol (0.039 g, 0.039 mmol) was dissolved in dichloromethane (10 mL). Trifluoromethanesulphonic acid (0.050 mL, 0.57 mmol) was added and after 5 min, a solution of tin(II) chloride (15 mg, 0.079 mmol) in THF (10 mL) was added. After stirring for an additional 7 min, the mixture was poured onto water/dichloromethane. The organic layer was dried (Na$_2$SO$_4$) and evaporated. Purification by preparative HPLC yielded 20 mg (49%) of the pure radical. ESR (acetonitrile, 200 G): singlet, linewidth 580 mG. Overhauser enhancement (acetonitrile): 120 at 10 W microwave power. MS (electrospray) m/z: 985 (M+H). Stability measurements: Half life in acetonitrile without exclusion of air: 26 h.

EXAMPLE 53

Tris-(8-dimethylaminocarbonyl-3,3,5,5-tetraoxo-2,2,6,6-tetra-methylbenzo[1,2-d:5,4-d']-bis(1,3)oxathiol-4-yl)methyl

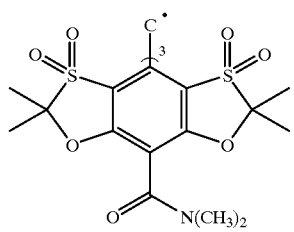

The reaction was performed under an argon atmosphere using deoxygenated solvents. Tris-(8-dimethylaminocarbonyl-2,2,6,6-tetramethylbenzo[1,2-d:5, 4-d']-bis(1,3)oxathiol-4-yl)methyl (0.020 g, 0.021 mmol) was dissolved in trifluoroacetic acid (2 mL) and H$_2$O$_2$ (0.4 mL, 35% in water) was added. After stirring overnight, the mixture was poured onto sat. NaCl/dichloromethane. The organic layer was washed with sat. NaCl and evaporated. Purification by preparative HPLC gave the pure radical. Yield: 0.005 g (25%) ESR (H$_2$O, 200 G): singlet, linewidth 470 mG. Overhauser enhancement (H$_2$O): 185 at 10 W microwave power. MS (electrospray) m/z: 1199 (M+Na), 1177 (M+H). Stability measurements: Half life in acetonitrile without exclusion of air: 26 h.

EXAMPLE 54

Tris-(8-ethoxycarbonylmethylthio-2,2,6,6-tetra-methylbenzo[1,2-d:5,4-d']-bis(1,3)oxathiol-4-yl) methanol

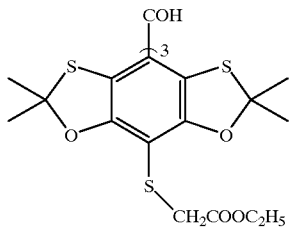

The reaction was performed under an argon atmosphere using deoxygenated solvents. Tris-2,2,6,6-tetramethylbenzo [1,2-d:5,4-d ]-bis(1,3)oxathiol-4-yl)methanol (1.0 g, 1.24 mmol) was dissolved in THF (25 mL). The mixture was cooled to −70° C. and n-butyllithium (5.8 mL, 1.6M in hexane) was added dropwise over 5 min, the cooling bath was removed and the mixture was left to attain ambient temperature over 30 min. The mixture was again cooled to −78° C. and sulfur (0.24 g, 7.5 mmol) was added. The cooling bath was removed and the mixture sonicated for 5 min and then left for 1 h. The mixture was dissolved by adding 2M NaOH (10 mL) followed by water (20 mL) and washed with diethyl ether, and then acidified with 4M HCl and taken up in diethyl ether. After drying ($Na_2SO_4$) and evaporation, the crude thiol was dissolved in acetonitrile (100 mL) and stirred with bromoethylacetate (1.25 mL) and $K_2CO_3$ (3 g) overnight. After evaporation and addition of dichloromethane the mixture was washed twice with water, dried ($Na_2SO_4$) and evaporated. Purification by preparative HPLC gave 0.60 g (42%) of the triester.

$^1$H NMR (DMF-$d_6$, 300 MHz) δ: 4.63 (s, 1H, OH), 4.11 (q, 6H, $CH_2$), 3.61 (d, 6H, CH,), 1.85–1.69 (m, 36H, $CH_3$), 1.26 (t, 9H, $CH_3$)

EXAMPLE 55

Tris-(8-ethoxycarbonylmethylthio-2,2,6,6-tetra-methylbenzo[1,2-d:5,4-d']-bis(1,3)oxathiol-4-yl) methyl

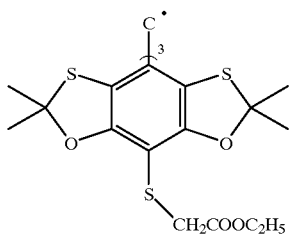

The reaction was performed under an argon atmosphere using deoxygenated solvents. Tris-(ethoxycarbonylmethylthio-2,2,6,6-tetramethylbenzo[1,2-d:5,4-d']-bis(1,3)oxathiol-4-yl)methanol (0.080 g, 0.070 mmol) was dissolved in dichloromethane (10 mL). $BF_3 \cdot Et_2O$ (0.140 mL, 1.11 mmol) was added and the mixture was stirred for 10 min. A solution of tin(II) chloride (40 mg, 0.22 mmol) in THF (4 mL) was added and after 1 h, the mixture was poured onto water/dichloromethane. The organic layer was washed with aq. $NaHCO_3$, dried ($Na_2SO_4$) and evaporated. Purification by preparative HPLC yielded 26 mg (33%) of the pure radical. ESR (acetonitrile, 200 G): singlet, linewidth 269 mG. MS (electrospray) m/z: 1125 ($M^+$).

EXAMPLE 56

Tris-(8-carboxylmethylthio-2,2,6,6-tetra-methylbenzo[1,2-d:5,4-d']-bis(1,3)oxathiol-4-yl) methyl

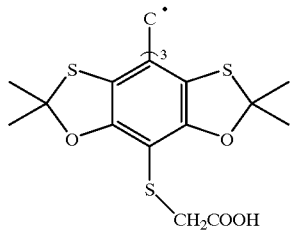

The reaction was performed under an argon atmosphere using deoxygenated solvents. Tris-(ethoxycarbonylmethylthio-2,2,6,6-tetramethylbenzo[1,2-d:5,4-d']-bis(1,3)oxathiol-4-yl)methyl (0.032 g, 0.028 mmol) was treated with methanol (3 mL) and 1% aqueous KOH (1 mL) for 30 min. The mixture was poured onto 1M NaOH/dichloromethane, the organic layer was discarded and the aqueous layer was carefully acidified and extracted with dichloromethane. The organic layer was washed with water, dried ($Na_2SO_4$) and evaporated. Purification by preparative HPLC yielded 0.020 g (60%) of the triacid radical. MS (electrospray) m/z: 1041 (M+H). ESR ($H_2O$, 200 G): singlet, linewidth 196 mG. Overhauser enhancement ($H_2O$, 1.1 mM): 156 at 1.1 W microwave power.

EXAMPLE 57

2,2,6,6-Tetra(ethoxycarbonyl)benzo[1,2-d:4,5-d']bis (1,3)dithiole

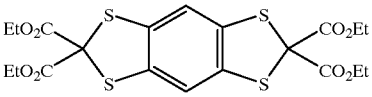

The reaction was performed under argon atmosphere using deoxygenated solvents. 1,2,4,5-Benzotetrathiole (1.50 g, 7.3 mmol) and $K_2CO_3$ (4 g) were mixed with dry DMF (70 ml) and a solution of dibromodiethyl malonate (4.26 g, 14.6 mmol) in DMF (15 ml) was added. The mixture was heated to 60° C. and stirred for 65 h. After cooling to room temperature, the reaction mixture was poured into ice water and then extracted with $CH_2Cl_2$ (2×100 ml). The combined organic phases were washed with water 4×50 ml), dried ($Na_2SO_4$) and evaporated. Yield: 3.32 g (88%).

$^1$H NMR (CDCl$_3$): 6.97 (s, 2H), 4.29 (q, J=7.2 Hz, 8H), 1.28 (t, J=7.2 Hz, 12H).

EXAMPLE 58

2,2,6,6-Tetra(methoxycarbonyl)-4,8-dibromobenzo[1,2-d:4,5-d']bis(1,3)dithiole

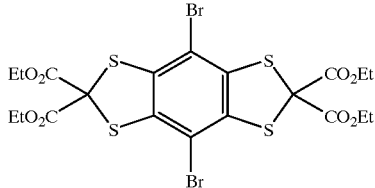

2,2,6,6-Tetra(ethoxycarbonyl)benzo[1,2-d:4,5-d']bis(1,3)-dithiole (10.7 g, 20.6 mmol) was dissolved in glacial acetic acid and bromine (16.5 g, 0.103 mol) was added. The solution was stirred at 65° C. for 17 h and aqueous $Na_2S_2O_3$ was added. The aqueous slurry was extracted with $CH_2Cl_2$ (3×100 ml), the combined organic phases were washed with water 3×50 ml), dried ($MgSO_4$) and evaporated. The residue was Triturated with $CH_3CN$ and dried. Yield: 10.1 g (72%).

$^1$H NMR (DMSO-$d_6$): 4.28 (q, J=7.2 Hz, 3H), 1.21 (t, J=7.2 Hz, 12H).

EXAMPLE 59

4,8-Dibromobenzo[1,2-d:4 5-d']bis(1,3)dithiole-2.6-dispiro-(4,4-dimethyl-3,5-dioxane)

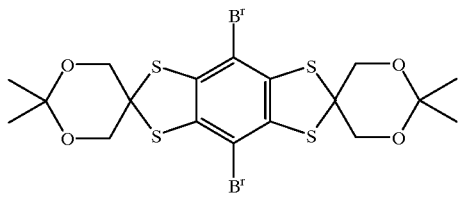

2,2,6,6-Tetra(methoxycarbonyl)-4,8-dibromobenzo[1,2-d:4,5-d']bis(1,3)dithiole (6.76 g, 10.0 mmol) was dissolved in dry THF, the solution was cooled to 0° C. and a solution of DIBAL in toluene (17.8 ml, 100 mmol) was added dropwise. The solution was heated to reflux temperature for 3 h and then allowed to cool to room temperature. Methanol (20 ml) was added dropwise followed by water (60 ml) and the pH was adjusted to 2 using aqueous 6M HCl. The solvents, except water, were removed by evaporation and the precipitate was collected by filtration. The product was washed with water, acetonitrile, dried and then suspended in dry acetone (600 ml). $BF_3.Et_2O$ (2.52 ml, 20 mmol) was added and the solution was stirred for 20 min. Solid $K_2CO_3$ (6.0 g) was added and stirring was continued for another 5 min. After filtering through a short pad of basic alumina, the solvents were removed by evaporation, the residue was triturated with $CH_2Cl_2$ and dried. Yield: 1.12 g (19%)

$^1$H NMR DMSO-$D_6$): 4.15 (S, 8H), 1.37 (S, 12H).

EXAMPLE 60

4-Bromobenzo[1,2-d:4,5-d']bis(1,3)dithiole-2,6-dispiro-(4,4-dimethyl-3.5-dioxane)

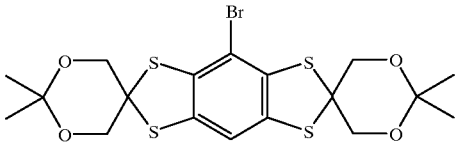

4,8-Dibromobenzo[1,2-d:4,5-d']bis(1,3)dithiole-2,6-dispiro-(4,4-dimethyl-3,5-dioxane) (1.14 g, 1.94 mmol) was dissolved in dry THF (270 ml) under an atmosphere of argon. After cooling the solution to −45° C., a solution of n-BuLi in hexane 2.5M, 2.02 mmol) was added dropwise. After stirring for 5 min, methanol (3 ml) was added, the solution was allowed to attain room temperature and the solvents were evaporated. The product was purified by chromatography on silica gel using a mixture of $CH_2Cl_2$ and methanol (99.5:0.5) as the eluent. Yield: 0.70 g (71%).

$^1$H NMR (CDCl$_3$): 6.80 (s, 1H), 4.15 s, 8H), 1.47 (s, 12 H).

EXAMPLE 61

Tris(benzo[1,2-d:4,5-d']bis(1,3)dithiole-4-yl-2,6-dispiro-(4,4-dimethyl-3,5-dioxane)methanol

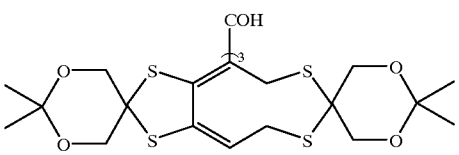

4-Bromobenzo[1,2-d:4,5-d']bis(1,3)dithiole-2,6-dispiro-(4,4-dimethyl-3,5-dioxane) (0.99 g, 1.94 mmol) was suspended in dry diethyl ether (28 ml) under an atmosphere of argon. A solution of n-BuLi (2.5M in hexane, 1.94 mmol) was added dropwise and, after 5 min, a solution of diethyl carbonate 0.078 ml, 0.64 mmol) in diethyl ether (3 ml) was added slowly. After stirring for 13 h, ethanol (5 ml) was added and the solvent was removed by evaporation. The product was purified by chromatography on silica gel using a mixture of $CHCl_3$ and ethyl acetate (20:1) as the eluent. Yield: 0.65 g (76%).

$^1$H NMR (CDCl$_3$): 7.16 (s, 3H), 6.01 (s, 1H), 3.86–4.22 (m, 24H), 1.43, 1.41, 1.37, 1.32 (4s, 36H).

EXAMPLE 62

Tris(8-ethoxycarbonylbenzo[1,2-d:4,5-d']bis(1,3)
dithiole-4-yl-2,6-dispiro-(4,4-dimethyl-3,5-dioxane))
methanol

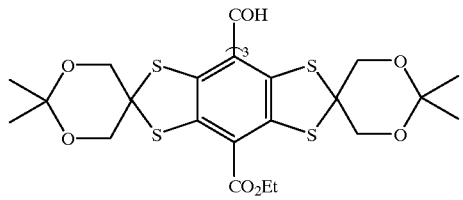

Tris(benzo[1,2-d:4,5-d']bis(1,3)dithiole-4-yl-2,6-dispiro-(4,4-dimethyl-3,5-dioxane))methanol (0.205 g, 0.156 mmol) was dissolved in dry benzene (12 ml) containing N,N,N',N'-tetramethylethylene diamine (0.33 ml, 2.18 mmol) under an atmosphere of argon. A solution of t-BuLi in pentane (1.5M, 2.18 mmol) was added dropwise and stirring was continued for 40 min. The solution was then transferred into another flask, kept at 0° C. and containing diethylpyrocarbonate (1.3 ml, 3.82 mmol) and benzene (6 ml). After stirring for 45 min, an aqueous $NaH_2PO_4$ buffer was added, the organic phase was separated, washed with water and evaporated. The product was purified by preparative HPLC. Yield: 55 mg (23%).

$^1$H NMR ($CDCl_3$): 6.68 (s, 1H), 4.41–4.52 (m, 6H), 3.86–4.21 (m, 24 H), 1.22–1.60 (m, 45H).

EXAMPLE 63

Tris(8-ethoxycarbonyl-2,2,6,6-tetrahydroxymethylbenzo[1,2-d:4,5-d']bis(1,3)
dithiole-4-yl)methanol

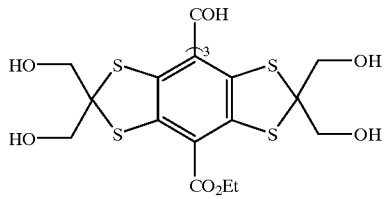

Tris(8-ethoxycarbonylbenzo[1,2-d:4,5-d']bis(1,3)dithiole-4-yl-2,6-dispiro-(4,4-dimethyl-3,5-dioxane))methanol (55 mg, 0.0359 mmol) was dissolved in a mixture of glacial acetic acid (20 ml) and water (5 ml) and the solution was stirred at room temperature for 42 h. The solvents were removed by evaporation, traces of acid were removed by addition of benzene followed by evaporation. HPLC analysis indicated >98 purity of the product. Yield: 42.4 mg (91%). MS (ESP$^-$, m/e): 1293 (M$^+$, 68%), 1291 ([M-2]$^-$, 100%).

EXAMPLE 64

Tris(8-carboxy-2,2,6,6-tetrahydroxymethylbenzo[1,2-d:4,5-d']bis(1,3)dithiole-4-yl)methyl Sodium Salt

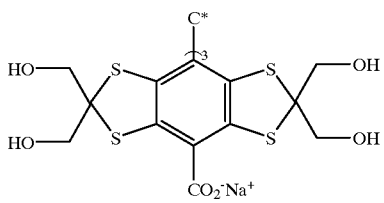

Tris (8-ethoxycarbonyl-2,2,6,6-tetrahydroxymethylbenzo[1,2-d:4,5-d']bis(1,3)dithiole-4-yl)methanol (3.4 mg, 0.0026 mmol) was dissolved in acetonitrile (2 ml) and the solution was cooled to 0° C. Trifluoromethanesulfonic acid (0.017 ml) was added and after 15 min, a solution of $SnCl_2$ (0.4 mg) in acetonitrile (1 ml) was added. After another 15 min, an aqueous $NaH_2PO_4$ buffer was added and the solvents were removed by evaporation. The residue was suspended in water and the pH was adjusted to 12 using an 1M aqueous NaOH solution. After stirring for 1 h, the solution was neutralized with 1M aqueous HCl and the solvent was removed by evaporation. The product was purified by preparative HPLC. Yield: 2.0 mg (60%). ESR (1.5 mM in $H_2O$, 100 G): singlet, linewidth 100 mG.

EXAMPLE 65

Tris(8-carboxy-2,2,6,6-tetra(hydroxyethoxy)
methylbenzo[1,2-d:4,5-d']bis(1,3)dithiole-4-yl)
methyl Sodium Salt

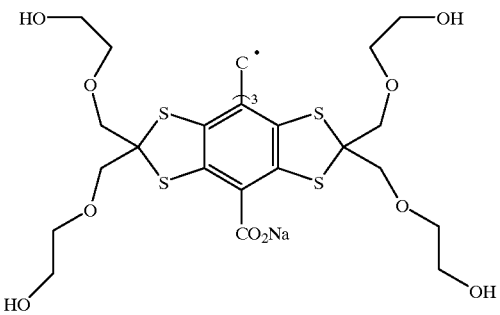

Tris(8-ethoxycarbonyl-2,2,6,6-tetra(hydroxyethoxy)methylbenzo[1,2-d:4,5-d']bis(1,3)dithiole-4-yl)methanol (see WO97/09633) (40 mg, 0.022 mmol) was dissolved in a mixture of acetic anhydride (S ml) and pyridine (10 ml) and the solution was stirred at room temperature for 2 hours. The organic solvents were removed by evaporation, the residue was dissolved in dichloromethane which was washed with water. After removal of the solvent by evaporation, the residue was dissolved in dichloromethane (8 ml) and then, a solution of trifluoromethanesulfonic acid in dichloromethane (0.58 mmol in 4 ml) was added at 0° C. After stirring for 2 minutes, a solution of $SnCl_2$ in acetonitrile (2 mg in 2 ml) was added and the solution was stirred for another minute. The reaction mixture was poured onto an aqueous pH 7 sodium phosphate buffer, the organic phase was separated and the aqueous phase was extracted with dichloromethane (25 ml). The combined organic phases were dried ($Na_2SO_4$) and the solvent was removed by evaporation. The residue was dissolved ethanol (10 ml) and 1M aqueous solution hydroxide (3 ml) was added. After stirring for 1 hour at room temperature, the pH was adjusted to 2 using 1M aqueous HCl and then the solution was subjected to purification by preparative HPLC (RP-18, $CH_3CN$-HCl (pH 2): 20:80). The fractions containing the pure product were combined and the acetonitrile was removed by evaporation. The residual aqueous solution was lyophilized, the residue was dissolved in water, the solution was neutralized using 1M aqueous NaOH and the solution was lyophilised again. Yield: 24 mg (62%). ESR: (1 mM in water, 100 G): singlet, linewidth 116 mG.

EXAMPLE 66

Benzo[1,2-d:4,5-d']bis(1,3)dithiole-2,2,6,6-tetraacetic Acid Ethyl Ester

The reaction was performed in dry flask under argon atmosphere. 1,2,4,5-Benzotetrathiole (74 g, 0.359 mol) and diethylacetone dicarboxylate (195.5 ml, 1.076 mol) were mixed with dichloromethane (3500 ml) and the mixture was cooled to −10° C. Fluoroboric acid (197.7 ml, 1.434 mol) was added and the cooling bath was changed to an icebath. The mixture was stirred at 0° C. for 90 minutes and then poured into solid sodium carbonate (300 g) under rigorous stirring. The slurry was filtered and the filtrate was evaporated to dryness. The solid residue was triturated with heptane (2×250 ml) and dried in a stream of air. Yield: 138.6 g (67%).

$^1$H NMR ($CDCl_3$): 6.97 (s, 2H), 4.16 (q, J=7. 2 Hz, 8H) 3.49 (s, 8H) 1.26 (t, J=7.2 Hz, 12H)

EXAMPLE 67

2,2,6,6-Tetra(hydroxyethyl)benzo[1,2-d:4,5-d']bis(1,3)dithiole

A dry flask under argon atmosphere was charged with diethyl ether (2600 ml) and $LiAlH_4$ (21.2 g 0.56 mol). Benzo[1,2-d:4,5-d']bis(1,3)dithiole-2,2,6,6-tetraacetic acid ethyl ester (80.2 g, 0.139 mol) was added and the mixture was refluxed for 26 h. The mixture was cooled to ambient temperature and ethanol (165 ml) was carefully added followed by water (410 ml). The ether was decanted off and the white precipitate was stirred with water (3300 ml) to give a slurry. After acidification with hydrochloric acid the slurry was filtered and the crude product was washed with water and dried. Yield: 55.0 g (97%)

$^1$H NMR (DMSO-$d_6$): 7.19 (s, 2H), 4.64 (t, J=5.7 Hz, 4H), 3.56 (q, J=5.7 Hz, 8H), 2.22 (t, J=6.3 Hz)

EXAMPLE 68

2,2,6,6-Tetra(t-butyoxyethyl)benzo[1,2-d:4,5-d']bis(1,3)dithiole

A dry flask under argon was charged with 2,2,6,6-tetra (hydroxyethyl)benzo[1,2-d:4,5-d']bis(1,3)dithiole (50.3 g, 0.124 mol), tetrahydrofuran (1200 ml) and isobutene (300 ml). Trifluoromethane sulphonic acid (21 8 ml, 0.248 mol) was added over 1 minute and the mixture was stirred for 1 h. The reaction mixture was poured into solid sodium carbonate (750 g) under vigorous stirring. After filtration through a silica pad the filtrate was evaporated to dryness and the solid residue was recrystallized from ethanol to give white needles. Yield: 61.6 g (79%).

$^1$H NMR ($CDCl_3$) 6.95 (s, 2H), 3.56 (t, J=6.6, 8H) 2.34 (t, J=6.6 Hz, 8H) 1.18 (s, 36H)

EXAMPLE 69

2,2,6,6-Tetra(t-butoxyethyl)4-iodo-benzo[1,2-d:4,5-d']bis(1,3)dithiole

A dry flask under argon was charged with 2,2,6,6-tetra(t-butoxyethyl)benzo[1,2-d:4,5-d']bis(1,3)dithiole (60.0 g, 95.08 mmol) and dry tetrahydrofuran (2000 ml). The mixture was cooled to −20° C. and n-Butyl lithium (76 ml of a 2.5M solution in hexane, 0.19 mol) was added over 3 minutes. The mixture was stirred for 20 minutes at −20° C. and then a solution of iodine (120 g, 0.475 mol) in tetrahydrofuran (500 ml) was added. The reaction mixture was poured into an aqueous sodium bisulphite solution and extracted with diethyl ether. The organic phase was washed once with an aqueous solution of sodium bisulphite and once with brine, dried ($MgSO_4$) and evaporated. The product was purified by chromatography on silica gel using a mixture of $CH_2Cl_2$ and ethyl acetate as the eluent. Yield: 36.7 g (51 i).

$^1$H NMR ($CDCl_3$) 6.87 (s, 1H), 3.57 (t, J=6.6 Hz, 8H) 2.35 (t, J=6.6 Hz 12 H).

EXAMPLE 70

Tris(2,2,6,6-tetra-(t-butoxy-ethyl)benzo[1,2-d:4,5-d']bis(1,3)dithiole-4-yl)methanol A dry flask under argon was charged with 2,2,6,6-tetra(t-butoxyethyl)4-iodo-benzo[1,2-d:4,5-d']bis(1,3)dithiole (29.0 g 38.3 mmol) and dry diethyl ether (520 ml). The mixture was cooled to −78° C. and n-butyl lithium (15.3 ml of a 2.5M solution in hexane, 38.3 mmol) was added and the cooling bath was removed. After 30 minutes an etherial solution (0.319M) of diethyl carbonate (40 ml, 12.76 mmol) was added dropwise over 120 minutes. Ten minutes after complete addition, the mixture was poured into aqueous $NaH_2PO_4$ and extracted with diethyl ether (2×250 ml). The organic phase was washed with water, dried ($MgSO_4$) and evaporated. The product was purified by chromatography on silica gel using a mixture of $CH_2Cl_2$ and acetonitrile as the eluent. Yield: 15.7 g (64%).

$^1$H NMR ($CDCl_3$): 7.07 (s, 3H), 6.57 (s, 1H), 3.30–3.60 (m, 24H), 2.10–2.50 (m, 24H), 1.12–1.17 (m, 108H).

EXAMPLE 71

Tris(8-hydroxycarbonyl-2,2,6,6-tetra-(t-butoxyethyl) benzo[1,2-d:4,5-d']-bis(1,3)dithiole-4-yl)methanol A dry flask under argon atmosphere was charged with N,N,N',N'-tetramethylethylene diamine (12.5 ml) and tris(2,2,6,6-tetra-(t-butoxyethyl)benzo[1,2-d:4,5-d']bis(1,3)dithiole-4-yl)methanol (960 mg, 0.5 mmol). The mixture was cooled to −20° C. and n-butyl lithium (3.0 ml of a 2.5M solution in hexane, 7.5 mmol) was added over 2 minutes. The mixture was allowed to reach ambient temperature and after 1 h the mixture was heated to 40° C. and kept at this temperature for 20 minutes. The mixture was then transferred to a dry flask containing an excess of carbon dioxide (s) and was then left to reach ambient temperature. The reaction mixture was taken up in water (200 ml) and ether (150 ml) and the phases were separated. The organic phase was extracted once more with water (100 ml) and the combined aqueous phases were acidified to pH 2 and extracted with ether (100 ml). The organic phase was dried ($MgSO_4$), evaporated and the product was purified by preparative HPLC. Yield: 315 mg (31%). $^1$H NMR (DMSO): 7.03 (s, 1H), 3.18–3.58 (m, 24H), 1.95–2.30 (m, 24 H), 0.96–1.09 (m, 108H).

EXAMPLE 72

Tris(8-carboxy-2,2,6,6-tetra-(hydroxyethyl)benzo[1,
2-d:4,5-d']bis(1,3)dithiole-4-yl)methyl Sodium Salt To a solution of trifluoromethane sulphonic acid (8.48 ml) in acetonitrile (64.0 ml) and dichloromethane (50.0 ml) at ambient temperature was added a solution of tris(8-hydroxycarbonyl-2,2,6,6-tetra-(t-butoxyethyl)benzo[1,2-d:4,5-d']bis(1,3)dithiole-4-yl)methanol (300 mg, 0.15 mmol) in acetonitrile (8.0 ml) and dichloromethane (8.0 ml). The mixture was stirred for 7 minutes and a 26 mM solution of tin chloride (5.2 ml, 0.14 mmol) was added. After 4 minutes ice cold 1M aqueous sodium hydroxide (96 ml) was added and the phases were separated and the aqueous phase containing .the product was collected. The pH was adjusted to pH 2 and the solution was subjected to preparative HPLC. The collected fractions was evaporated to eliminate acetonitrile and the aqueous solution was poured on a pad packed with C-18 material. The pad was washed with deionized water and the product was eluted with ethanol and evaporated to dryness. To the residue was added water (5 ml) and the pH was carefully adjusted to pH 7 with diluted hydrochloric acid and the mixture was lyophilized. Yield: 37.6 mg (18%) ESR (1.0 mM in $H_2O$, 100 G): singlet, linewidth 160 mG.

EXAMPLE 73

Tris(8-carboxymethylthio-2,2,6,6-tetra-(2-(1-t-butyoxyethyl))benzo[1,2-d:4,5-d']bis(1,3)dithiole-4-yl)methanol A dry flask was charged with tris(2,2,6,6-tetra-(2-(1-t-butoxyethyl))benzo[1,2-d:4,5-d']bis(1,3)dithiole-4-yl)methanol (1.0 g, 0.521 mmol) and N,N,N',N'-tetramethyl-ethylenediamine (TMEDA, 10.4 ml). The solution was stirred at −20° C. and s-BuLi (6 ml, 7.8 mmol) was added dropwise. The temperature was adjusted to −10° C., kept there for 14 minutes, and then adjusted to −25° C. sulphur (0.58 g, 18.1 mmol) was added and the cooling bath was removed. After 90 minutes the reaction mixture was evaporated to dryness. The residue was treated with 2M HCl (50 ml) and $CH_2Cl_2$ (40 ml). The organic phase was dried ($Na_2SO_4$) and evaporated to dryness. Ethanol (99.5%, 40 ml), $K_2CO_3$ (4 g, 28.9 mmol), ethyl bromoacetate (1.73 g, 10.4 mmol) were added to the residue The suspension was stirred for 2 hours, filtered and evaporated to dryness. The residue was washed with methanol/water (90/10, v/v, 20 ml) and dried. Ethanol (25 ml) and 2M KOH (10 ml) were added, and, after stirring for one hour, the pH was adjusted to 4.5 using 2M HCl. The precipitate was filtered off and then dissolved in diethyl ether (250 ml). Water (300 ml) was added and pH was adjusted to 10.2 using 2M HCl. The aqueous phase was isolated, pH was adjusted to 2.5 using 2M Hal and the product was extracted into diethyl ether (100 ml). After evaporation, 0.58 g (51%) of the product remained with a purity of 90% as ascertained by HPLC analysis. MS (ESP, m/e): 2187.2 (M-2).

EXAMPLE 74

Tris(8-carboxymethylthio-2,2,6,6-(2-(1-hydroxyethyl))benzo[1,2-d;4,5-d']bis(1,3)dithiole-4-yl)methyl Sodium Salt A flask was charged with tris(8-carboxymethylthio-2,2,6,6-tetra-(2-(1-t-butoxyethyl))benzo-[1,2-d-4,5-d']bis(1,3) dithiole-4-yl)methanol (0.452 g, 0.244 mmol) and formic acid (25 ml). The solution was left overnight and then evaporated to dryness. The residue was dissolved in acetonitrile (17 ml) and trifluoromethane-sulfonic acid (0.215 ml, 2.44 mmol) was added. After stirring for two minutes, tin(II)chloride (26.8 mg, 0.141 mmol) dissolved in acetonitrile (2.7 ml) was added. After stirring for another 1.5 minutes, the reaction mixture was poured into stirred water (500 ml). The solution was extracted with ethyl acetate (200 ml) and the organic phase was washed with water (50 ml), dried ($Na_2SO_4$) and evaporated to dryness. The product was purified by preparative HPLC (RP-18, $CH_3CN$/aqueous 0.01M HCl 20:80). After removal of the solvents, the acid was neutralized with 1M aqueous NaOH and the solution was then lyophilized. Yield: 0.172 g (45%). MS (ESP, m/e): 1499 (M$^-$) ESR (100 G, 2.5 mM aqueous solution): singlet, linewidth 195 mG.

EXAMPLE 75

Tris(8-[N,N-bis(2,2-dimethyl-1,3-dioxolane-4-methyl)aminocarbonylmethylthio]-2,2,6,6-tetra-(2-(1-t-butoxyethyl))benzo[1,2-d:4,5-d']bis(1,3) dithiole-4-yl)methanol A dry flask was charged with tris(2,2,6,6-tetra-(2-(1-t-butoxyethyl))benzo[1,2-d:4,5-d']bis(1,3)dithiole-4-yl) methanol (3.0 g, 1.56 mmol) and TMEDA (31.2 ml). The solution was stirred at −20° C. and sec-BuLi (18 ml, 23.4 mmol) was added dropwise. The temperature was adjusted to −10° C. and kept there for 14 minutes and then adjusted to −25° C. Sulphur (1.74 g, 54.4 mmol) was added and the cooling bath was removed. After 90 minutes, the reaction mixture was evaporated to dryness. The residue was treated with 2M aqueous HCl (100 ml) and dichloromethane (100 ml). The organic phase was dried ($Na_2SO_4$) and evaporated to dryness. Ethanol (99.5%, 80 ml), $K_2CO_3$ (8 g, 57.9 mmol) and 2-bromo-N,N-bis(2,2-dimethyl-1,3-dioxolane-4-methyl)-acetamide (5.14 g, 14.0 mmol) were added to the crude intermediate. The resulting suspension was stirred for 20 hours at room temperature, filtered and evaporated to dryness. Purification was performed by preparative HPLC (RP-18, $CH_3CN/CH_2Cl_2$, 3:1) Yield: 1.68 g (37.5%). MS (ESP, m/e): 2869 (M$^+$)

EXAMPLE 76

Tris(8-[N,N-bis(2,3-dihydroxypropyl)aminocarbonylmethylthio]-2,2,6,6-tetra-(2-(1-hydroxyethyl))benzo[1,2-d:4,5d']bis(1,3)dithiole-4-yl)methyl A flask was charged with tris(8-[N,N-bis(2,2-dimethyl-1,3-dioxolane-4-methyl)aminocarbonylmethylthio]-2,2,6,6-(2-(1-t-butoxyethyl))benzo[1,2-d:4,S-d']bis(1,3)dithiole-4-yl)methanol (0.50 g, 0.174 mmol) and dichloromethane (46 ml) at room temperature. To the stirred solution was added a solution of trifluoromethanesulfonic acid (0.62 ml) in dichloromethane (46 ml). After stirring for two minutes, a solution of tin(II)chloride (33 mg, 0.174 mmol) in acetonitrile (4.6 ml) was added. The reaction mixture was poured into water (460 ml) after another 2 minutes. The radical was purified by preparative HPLC (RP-18, $CH_3CN$/water, 5:95), neutralized with 1M NaOH and lyophilized. Yield: 200 mg (59%). MS (ESP, m/e): 1941 ((M+1)$^+$). ESR (100 G, 1 mM in water): singlet, linewidth 274 mG.

EXAMPLE 77

Benzo[1,2-d:4,5-d']bis(1,3)dithiole-2,2,6,6-tetraacetic Acid Methyl Ester

The reaction was performed in a dry flask under argon atmosphere. 1,2,4,5-Benzotetrathiol 20.45 g, 0.097 mol) and dimethylacetone dicarboxylate (50.68 g, 0.291 mol) were mixed with dichloromethane (250 ml) and the mixture was cooled to −10° C. Fluoroboric acid etherate (53 ml, 0.388 mol) was added and the cooling bath was changed to an ice bath. The mixture was stirred at 0° C. for 90 minutes and then poured into solid sodium carbonate (100 g) under vigorous stirring. The slurry was filtered and the filtrate was evaporated to dryness. The solid residue was triturated with diethyl ether (300 ml) and dried in a stream of air. Yield: 30.4 g (60 !).

$^1$H NMR (CDCl$_3$, 300 MHz) δ: 6.97 (s, 2H), 3.70 (s, 12H) 3.51 (s, 8H).

EXAMPLE 78

4,8-Dibromobenzo[1,2-d:4,5-d']bis(1,3)dithiole-2,2,6,6-tetraacetic Acid Methyl Ester A flask was charged with benzo[1,2-d:4,5-d']bis(1,3)dithiole-2,2,6,6-tetraacetic acid methyl ester (30 g, 0.058 mol) and dichloromethane (300 ml). Iodine (14.7 g, 0.0578 mol) and iodine monobromide (83.7 g, 0.405 mol) were added and the mixture was heated to reflux for 3 hours The mixture was cooled and poured into a stirred solution of ethanol (75 ml) and sodium bisulphite (75 g) in water (600 ml). The organic phase was separated, 100 ml water was added and the biphasic mixture was evaporated in vacuo to remove dichloromethane. The resulting aqueous slurry was filtered and the filter cake was washed with water (3×200 ml) and recrystallized from n-butanol (450 ml). Yield: 31.8 g (81%).

$^1$H NMR (CDCl$_3$, 300 MHz) 3.72 (s, 12H), 3.55 (s, 8H)

EXAMPLE 79

4,8-Dibromobenzo[1,2d:4,5-d']bis(1,3)dithiole-2,2,6,6-tetraacetic-2-d$_2$-acid Methyl Ester A dry flask was charged with THF (120 ml) and methanol-d$_1$ (200 ml). Sodium (0.64 g, 0.0278 mol) was dissolved in the mixture and 4,8-dibromobenzo[1,2-d:4,5-d']bis(1,3)dithiole-2,2,6,6-tetraacetic acid methyl ester (40.0 g, 0.0546 mol) was added. The mixture was heated to reflux for 12 hours and then evaporated in vacuo. The residue was suspended in aqueous 0.1M NaH$_2$PO$_4$ (500 ml) and the slurry was filtered and washed with aqueous 0.1M NaH$_2$PO$_4$ (2×50 ml) The product was dried in a stream of air. Yield: 31.1 g (83%).

$^1$H NMR (CDCl$_3$, 300 MHz): 3.72 (s, 12H).

EXAMPLE 80

2,2,6,6-Tetra(2-(1-hydroxy-2,2-d$_2$-ethyl))-4,8-dibromobenzo[1,2-d:4,5-d']bis(1,3)dithiole A flask under an argon atmosphere fitted with a reflux condenser was charged with THF (210 ml) and lithium borohydride (3.22 g, 0.15 mol). Methanol (5.99 ml, 0.15 mol) was added dropwise while stirring and 15 minutes after the complete addition 4,8-dibromobenzo[1,2-d:4,5-d']bis(1,3)dithiole-2,2,6,6-tetraacetic-2-d$_2$-acid methyl ester (20 g, 0.0296 mol) was added in portions under 15 minutes. The mixture was then stirred for 2 hours and then heated to reflux for an additional 2 hours. After cooling to ambient temperature, the reaction was quenched by the dropwise addition of 20t aqueous acetic acid (75 ml) The mixture was evaporated in vacuo to remove THF and the pH was adjusted to 3 using 3M hydrochloric acid. The obtained slurry was filtered and the filtercake was washed with water (3×100 ml) and dried in a stream of air. Yield: 16.4 g, (98%)

$^1$H NMR (CDCl$_3$, 300 MHz): 4.71 (broad s, 4H), 3.57 (s, 8H).

EXAMPLE 81

2,2,6,6-Tetra(2-(1-hydroxy-2,2-d$_2$-ethyl))-4-bromobenzo[1,2-d:4,5-d']bis(1,3)dithiole A flask was charged with dimethyl formamide (290 ml) and 2,2,6,6-tetra(2-(1-hydroxy-2,2-d$_2$-ethyl))-4,8-dibromobenzo[1,2-d:4,5-d']bis(1,3)dithiole (32 g, 0.056 mol). The starting material was dissolved with gentle heating and the solution was cooled to ambient temperature. Zn (7.5 g, 0.115 mol), CuSO$_4$. 5 H$_2$O (5.7 g, 0.023 mol) and ammonium formate (39.7 g, 0.629 mol) were added to the vigorously stirred reaction mixture. After 50 minutes the mixture was filtered and the filtrate was poured into water (1500 ml) and the pH was adjusted to 4 using 3M hydrochloric acid. The precipitate was filtered off and washed with water (2×300 ml) and diethyl ether (2×60 ml). The crude material was recrystallized from a mixture of ethanol and water (1:1) and dried in vacuo. Yield: 18.1 g, (70%).

$^1$H NMR (CDCl$_3$, 300 MHz): 7.18 (s, 1H), 4.66 (t, J=5.1 Hz, 4H) 3.55 (d, J=5.1 Hz, 8H).

EXAMPLE 82

2,2,6,6-Tetra(2-(1-t-butoxy-2,2-d$_2$-ethyl))-4-bromobenzo[1,2-d:4,5-d']bis(1,3)dithiole A dry flask under argon was charged with 2,2,6,6-tetra(2-(1-hydroxy-2,2-d$_2$-ethyl))-4-bromobenzo[1,2-d:4,5-d']bis(1,3)dithiole (31.0 g, 0.063 mol), THF (300 ml) and the headspace was flushed with isobutene. Trifluoromethane sulphonic acid (3.0 ml, 0.0349 mol) was added to the stirred mixture and a slight pressure of isobutene was applied to the flask. The mixture was stirred for 4.5 hours and then poured into a mixture of aqueous 1M NaOH (40 ml) and water (300 ml). The phases were separated and the organic phase was diluted with diethyl ether (150 ml) and was washed with water (3×200 ml). The organic phase was dried (MgSO$_4$) and evaporated and the crude product was dissolved in heptane (100 ml) and poured on a silica pad (300 g). The pad was eluted with a mixture of heptane and ether (4:1, v/v) and the eluate was evaporated to yield a white waxlike solid. Yield: 33 8 g, (75%).

$^1$H NMR (CDCl$_3$, 300 MHz): 6.85 (s, 1H), 3.56 (s, H), 1.18 (s, 36H).

EXAMPLE 83

Tris(2,2,6,6-tetra(2-(1-t-butoxy-2,2-d$_2$-ethyl))benzo[1,2-d:4,5-d']bis(1,3)dithiole-4-yl)methanol A dry flask under argon was charged with 2,2,6,6-tetra(2-(1-butoxy-2,2-d$_2$-ethyl) )-4-bromo-benzo[1,2-d:4,5-d']bis(1,3)dithiole (10.0 g, 0.0139 mol) and dry diethyl ether (140 ml). The mixture was cooled to −20° C. and n-butyl lithium (5.6 ml of a 2.5M solution in hexane, 0.014 mol) was added and the cooling bath was removed. After 30 minutes, a solution of diethyl carbonate (546 mg, 4.63 mmol) in diethyl ether was added dropwise over 2 hours. After complete addition the mixture was stirred for an additional 10 minutes and then poured into an aqueous solution of NaH$_2$PO$_4$ (125 ml, 0.2M) The phases were separated and the organic phase was washed twice with brine and dried over MgSO$_4$. The organic phase was evaporated and the red oily residue was dissolved in ethanol (56 ml) and left over night. The following day the yellow crystalline product was collected and dried in vacuo. Yield: 5.s4 g, (62%).

¹H NMR (CDCl₃, 300 MHz): 707 (s, 3H), 6.57 (s, 1H), 3.60–3.30 (m. 24H), 1.18–1.04 (m, 108H).

EXAMPLE 84

Tris(8-carboxyl-2,2,6,6-tetra(2-(1-t-butoxy-2,2-d₂-ethyl))-benzo[1,2-d:4,5-d']bis(1,3)dithiole-4-yl) methanol A dry flask under argon was charged with TMEDA (89 ml) and tris(2,2,6,6-tetra(2-(1-t-butoxy-2,2-d₂-ethyl))-benzo[1,2-d:4,5-d']bis(1,3)dithiole-4-yl)methanol (8.65 g, 4.45 mmol). The mixture was cooled to −20° C. and sec-BuLi (51.5 ml, 0.067 mol, 1.3M in cyclohexane) was added over 4 minutes while the temperature was kept below −10° C. After complete addition the reaction mixture was stirred at −10° C. for 25 minutes and then transferred onto solid CO₂ and left to attain ambient temperature. The thick mixture was taken up in diethyl ether (445 ml) and water (445 ml) and acidified with 6M hydrochloric acid to pH 1.5. The phases were separated and the aqueous phase was extracted once more with diethyl ether (445 ml). The combined organic phase were dried (MgSO₄) and evaporated to dryness to give a yellow foam. Yield: 5.80 g (63%).

¹H NMR (CD₃CN, 300 MHz): 7.18 (s, 1H), 3.60–3.25 (m, 24H), 1.15–1.02 (m, 108H).

EXAMPLE 85

Tris(8-carboxyl-2,2,6,6-tetra(2-(1-hydroxy-2,2-d₂-ethyl))benzo[1,2-d:4,5-d']bis(1,3)dithiole-4-yl) methyl A flask was charged with tris(-carboxy-2,2,6,6-tetra(2-(1-t-butoxy-2,2-d₂-ethyl))-benzo[1,2-d:4,5-d']bis(1,3)dithiole-4-yl)methanol (5.80 g, 0.0028 mol) and formic acid (60 ml) and the mixture was stirred over night. The mixture was evaporated to dryness, the residue was dissolved in acetonitrile (30 ml) and again evaporated to dryness. The residue was dissolved in acetonitrile (12 ml) and a( solution of trifluoromethane sulphonic acid (4.87 ml, 0.0558 mol) in acetonitrile (22.5 ml) was added while stirring. After 6 minutes, a solution of SnCl2 (0.529 g, 0.00279 mol) in THF (2.87 ml) was added to the stirred reaction mixture. After stirring for 2 minutes, ethyl acetate (29 ml) was added directly followed by an addition of aqueous NaH₂PO₄ (140 ml, 2M). The biphasic mixture was stirred vigorously for 5 minutes and the phases were separated. The organic phase was evaporated and treated with aqueous sodium hydroxide (55.8 ml, 1M). After 15 minutes the aqueous phase was added dropwise into hydrochloric acid (112 ml 1.5M). After 15 minutes the dark precipitate was collected and washed with diluted hydrochloric acid (2×10 ml, 0.1M) followed by diethyl ether (10 ml). Yield: 3.56 g, (92%).

EXAMPLE 86

Tris(8-carboxyl-2,2,6,6-tetra(2-(1-hydroxy-2,2-d₂-ethyl))-benzo[1,2-d:4,5-d']bis(1,3)dithiole-4-yl) methyl Sodium Salt To a sample of the solid radical triacid, obtained in Example 85, water was added and the solution was neutralized to pH 7 using 0.05M sodium hydroxide and the solution was lyophilized. ESR (1.0 mM in H₂O, 100 G): singlet, linewidth 70 mG.

EXAMPLE 87

N,N-Bis(2,2-dimethyl-1,3-dioxolane-4-methyl)-2-bromo-acetamide

A flask was charged with N,N-bis(2,3-dihydroxyprop-1-yl)-amine (30.0 g, 0.1816 mol), 2,2-dimethoxypropane (120 ml), dimethyl formamide (100 ml) and concentrated sulphuric acid (20 ml). The mixture was stirred overnight and then poured into a mixture of saturated NaHCO₃ (500 ml) and sodium hydroxide (16. 0 g, 0.4 mol) while stirring. The aqueous phase was extracted with diethyl ether (3×200 ml) and the organic phase was dried (MgSO,) and evaporated to give a pale yellow oil. The oil was dissolved in a mixture of dichloromethane (75 ml) and 0.03M aqueous sodium hydroxide (2000 ml). A solution of bromoacetyl bromide (11.81 g, 0.0585 mol) in dichloromethane (75 ml) was added dropwise over 20 minutes and the pH of the reaction mixture was continuously monitored during the addition and was kept close to 7 by addition of 1M aqueous sodium hydroxide. After complete addition the organic phase was separated and washed with water (2×150 ml), dried (MgSO₄) and evaporated to give a pale yellow oil. Yield: 30.7 g (79%)

¹H NMR (CDCl₃, 300 MHz): 4.35–4.25 (m, 2H) 4.16–4.02 (m, 3H), 3.93–3.85 (m, 2H), 3.75–3.55 (m, 4H), 3.25–3.17 (m, 1H), 1.42–1.40 (m, 6H), 1.33–1.31 (m, 6H).

EXAMPLE 88

Tris(8-carboxyl-2,2,6,6-tetra(hydroxyethyl)-benzo[1,2-d:4,5-d']bis(1,3)dithiole-4-yl)methyl N,N-bis(1,2-dihydroxyprop-3-yl)-acetamid-2-yl-ester A flask was charged with dimethyl formamide (600 ml) and tris(8-carboxyl-2,2,6,6-tetra(hydroxyethyl)-benzo[1,2-d:4,5-d']-bis(1,3)dithiole-4-yl)methyl sodium salt (2.57 g, 1.8 mmol). N,N-bis(2,2-dimethyl-1,3-dioxolane-4-methyl)-2-bromo-acetamide (6.60 g, 18 mmol) was added followed by a second portion (6.60 g, 18 mmol) after 15 minutes. The mixture was stirred for 60 minutes and the solvent was removed by evaporation. The residue was dissolved in a mixture of acetonitrile (100 ml) and water (150 ml) and 2M hydrochloric acid (10 ml) was added. After 2 hours the acetonitrile was removed by evaporation and the product was purified by preparative HPLC. Yield: 2.70 g (76%). ESR (1.0 mM in H₂O, 100 G): singlet, linewidth 226 mG.

We claim:
1. A radical compound of formula I

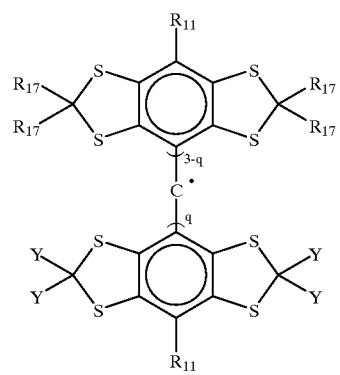

wherein:
  each $R_{11}$ which may be the same or different and represents a hydrogen atom or a group of formula -M or -XM;
  each X which may be the same or different represents an oxygen or sulphur atom or a group CO or $S(O)_n$ (where n is 1 to 3);
  M represents a water solubilizing group;
  each $R_{17}$ which may be the same or different represents a hydrogen atom, or a hydrocarbon group, or a water solubilizing group M or two groups $R_{17}$ together with the atom to which they are bound represent a carbonyl group or a 5 to 8 membered cycloalkylidene, mono- or di-oxacycloalkylidene, mono- or di-azacycloalkylidene or mono- or di-thiacycloalkylidene group and $R_{17}$ where it is other than hydrogen, is optionally substituted by a hydroxyl group, an optionally alkoxylated, optionally hydroxylated acyloxy or alkyl group or a water solubilizing group M;

q denotes 1, 2 or 3; and each group Y which may be the same or different denotes group $R_{17}$ with the proviso that at least one group Y is a hydroxylated or alkoxylated $C_{2-6}$-alkyl group or a deuterated analog thereof or a deuterated analog, precursor or salt thereof.

2. A radical compound as claimed in claim 1 wherein at least one group Y is a $CH_2COOR$, group (wherein $R_{22}$ is hydrogen or a $C_{1-6}$-alkyl group).

3. A radical compound as claimed in claim 2 wherein each group Y is a $CH_2CH_2OR_{22}$ group.

4. A radical compound as claimed in claim 3 wherein $R_{22}$ is hydrogen or t-Bu.

5. A radical compound as claimed in any of claims 1 or 2 to 4 wherein q denotes 3.

6. A radical compound as claimed in claim 1 being

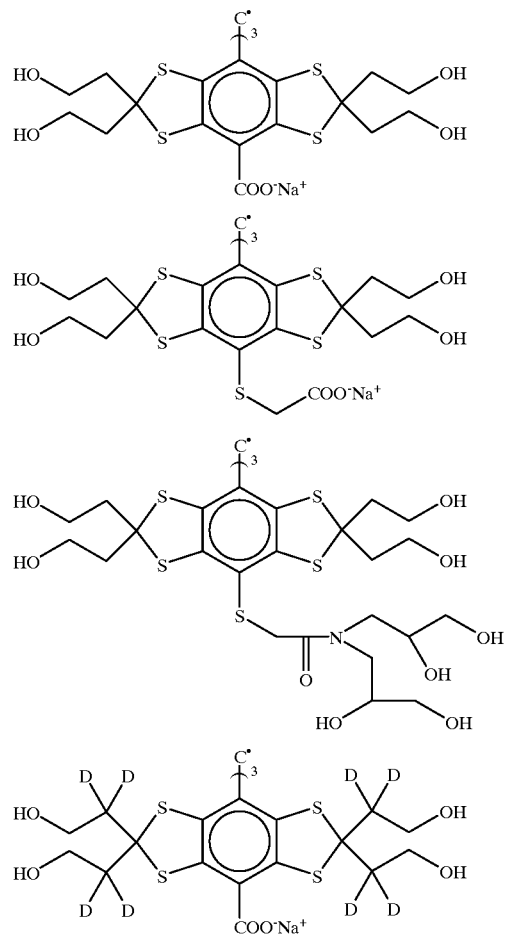

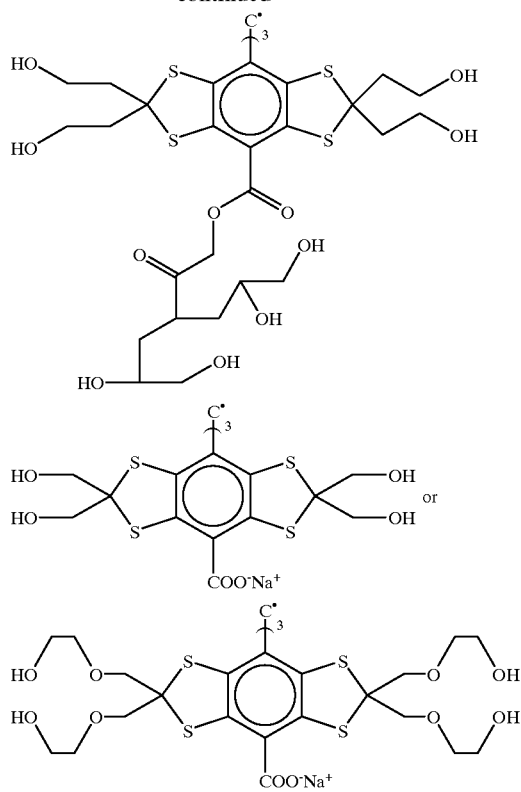

7. A radical compound of formula

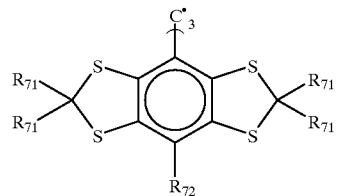

wherein each $R_{71}$ is an optionally deuterated, hydroxylated $C_{1-4}$ alkyl or oxaalkyl group; and $R_{72}$ is a group $-(S)_a-(CH_2)_b-COX^*$ where a and b are each 0 or 1 and $X^*$ is hydroxyl, $N(R_{73})_2$ or $OR_{74}$ or a salt thereof, $R_{73}$ is hydrogen or hydroxy $C_{1-4}$ alkyl and $R_{74}$ is (hydroxy $C_{1-4}$ alkyl) aminocarbonylmethyl.

8. A magnetic resonance imaging contrast medium comprising a radical compound as claimed in any of claims 1 or 2 to 7 together with at least one pharmacologically acceptable carrier or excipient.

9. A method of magnetic resonance Investigation of a sample, said method comprising introducing into said sample a radical compound as claimed in any of claims 1 or 2 to 7, exposing said sample to a first radiation of a frequency selected to excite electron spin transitions in said radical, exposing said sample to a second radiation of a frequency selected to excite nuclear spin transitions in selected nuclei in said sample, detecting free induction decay signals from said sample, and, optionally, generating an image or dynamic flow data from said detected signals.

10. A method for determining oxygen concentration in a sample, said method comprising the following steps:

introducing into said sample an effective amount of a physiologically tolerable radical compound as claimed in any of claim 1 or 2 to 7;

irradiating said sample with radiation of an amplitude and frequency selected to stimulate an electron spin resonance transition of said radical;

detecting electron spin resonance enhanced magnetic resonance signals from said sample under at least first, second and third conditions, whereby under said first and second conditions said radiation is of a first frequency, under said third conditions said radiation is of a second frequency different from said first frequency, under said first, second and third conditions said radiation is of a first, second and third amplitude, said first and second amplitudes at least being different from each other; and manipulating said detected signals whereby to determine oxygen concentration in said sample.

11. A method as claimed in claim 10 comprising:

(a) introducing a radical compound as claimed in any one of claims 1 or 2 to 7 into body tissue or the vasculature;

(b) generating a first OMRI image of said sample at VHF power $P_A$, irradiation period $T_{VHF1}$ and on resonance;

(c) generating a second OMRI image of said sample at a second VHF power $P_B$, irradiation time $T_{VHF1}$ and on-resonance;

(d) generating a third OMRI image of said sample at VHF power $P_C$, irradiation time $T_{VHF1}$ and off-resonance;

(e) manipulating the images obtained in steps (b) to (d) and calibrating using parameters determined ex vivo to provide an oxygen image of said sample.

12. A method as claimed in claim 11 wherein a fourth and fifth image are generated in the imaging sequence.

13. A process for preparing a radical compound as claimed in any of claims 1 or 2 to 7 comprising subjecting a radical precursor therefor to a radical generation step and optionally subsequently modifying the substitution on the aryl moieties.

* * * * *